(12) United States Patent
Milne et al.

(10) Patent No.: US 11,064,694 B2
(45) Date of Patent: Jul. 20, 2021

(54) DEVICE AND METHOD FOR HEATING OR COOLING A SAMPLE

(71) Applicant: CELL THERAPY CATAPULT LIMITED, London (GB)

(72) Inventors: Stuart Milne, Cambridge (GB); Alex Nancekievill, Cambridge (GB); Christopher Creasey, Cambridge (GB); Stephen Lamb, Potters Bar (GB); Rupert Rutledge, Hitchen (GB)

(73) Assignee: CELL THERAPY CATAPULT LIMITED, London (GB)

( * ) Notice: Subject to any disclaimer, the term of this patent is extended or adjusted under 35 U.S.C. 154(b) by 106 days.

(21) Appl. No.: 16/083,812

(22) PCT Filed: Mar. 9, 2017

(86) PCT No.: PCT/GB2017/050634
§ 371 (c)(1),
(2) Date: Sep. 10, 2018

(87) PCT Pub. No.: WO2017/153761
PCT Pub. Date: Sep. 14, 2017

(65) Prior Publication Data
US 2019/0075786 A1   Mar. 14, 2019

(30) Foreign Application Priority Data
Mar. 9, 2016 (GB) ..................... 1604062

(51) Int. Cl.
*A01N 1/02* (2006.01)
*B01L 7/00* (2006.01)
(Continued)

(52) U.S. Cl.
CPC .......... *A01N 1/0257* (2013.01); *A01N 1/0252* (2013.01); *A61M 1/0272* (2013.01);
(Continued)

(58) Field of Classification Search
CPC .......... B01L 2200/025; B01L 2200/147; B01L 2300/0829; B01L 2300/1822;
(Continued)

(56) References Cited

U.S. PATENT DOCUMENTS

| 6,555,792 B1 * | 4/2003 | Elsener ............... B01J 19/0093 219/428 |
| 8,709,364 B2 * | 4/2014 | Osaka .................. G01N 35/025 422/562 |

(Continued)

FOREIGN PATENT DOCUMENTS

| EP | 1088590 A1 | 4/2001 |
| EP | 3085445 A1 | 10/2016 |

(Continued)

OTHER PUBLICATIONS

British Search Report issued in British Application No. GB1604062.8 dated Aug. 24, 2016.

(Continued)

*Primary Examiner* — Natalie Huls
(74) *Attorney, Agent, or Firm* — Jeff B. Vockrodt; Culhane Meadow, PLLC

(57) ABSTRACT

A sample heating/cooling device comprises a plurality of members operable in use to heat and/or cool one or more samples. Each member has a sample contact surface and is biased towards a resting position under the operation of a biasing means. The members are movable independently of one another against said bias under the application of a force on the sample contact surface and so are able to conform to the shape of a sample placed on the members to provide a uniform heating/cooling profile. The members may be mounted in a heating/cooling element and adapted to conduct thermal energy between the sample and the element. The device is particularly suitable for thawing frozen sample (Continued)

bags having an irregular shape. A corresponding method is also described.

30 Claims, 12 Drawing Sheets

(51) Int. Cl.
  *F28D 11/08*  (2006.01)
  *F28F 5/00*  (2006.01)
  *A61M 1/02*  (2006.01)
  *B01J 19/00*  (2006.01)
  *B01L 3/00*  (2006.01)

(52) U.S. Cl.
  CPC ............... *B01J 19/00* (2013.01); *B01L 3/505* (2013.01); *B01L 7/00* (2013.01); *F28D 11/08* (2013.01); *F28F 5/00* (2013.01); *B01J 2219/00087* (2013.01); *B01J 2219/00961* (2013.01); *B01L 2300/0829* (2013.01); *B01L 2300/185* (2013.01); *B01L 2300/1822* (2013.01); *B01L 2300/1827* (2013.01); *B01L 2300/1894* (2013.01)

(58) Field of Classification Search
  CPC ....... B01L 2300/1827; B01L 2300/185; B01L 2300/1894; B01L 7/52; A01N 1/0252; A01N 1/0257; A01M 1/0272; F28F 5/00
  See application file for complete search history.

(56) References Cited

U.S. PATENT DOCUMENTS

| | | | |
|---|---|---|---|
| 2002/0028507 A1* | 3/2002 | Heimberg | B01L 3/50853 435/305.3 |
| 2004/0065655 A1 | 4/2004 | Brown et al. | |
| 2004/0112969 A1 | 6/2004 | Saga et al. | |
| 2007/0077648 A1 | 4/2007 | Okamoto et al. | |
| 2010/0104485 A1 | 4/2010 | Yuan | |
| 2010/0281886 A1* | 11/2010 | Shaham | A01N 1/0263 62/51.1 |
| 2015/0079666 A1* | 3/2015 | Brahmasandra | C23C 14/24 435/287.2 |
| 2017/0007999 A1* | 1/2017 | Aranburu Lazcano | B01L 7/52 |

FOREIGN PATENT DOCUMENTS

| | | |
|---|---|---|
| JP | 2004518129 A | 6/2004 |
| JP | 2007061245 A | 3/2007 |
| WO | 02057798 A2 | 7/2002 |
| WO | WO 02/081076 A2 | 10/2002 |
| WO | WO 2004/102088 A1 | 11/2004 |
| WO | WO 2014/102403 A1 | 7/2014 |
| WO | WO 2015/092080 A1 | 6/2015 |

OTHER PUBLICATIONS

British Search Report issued in British Application No. GB1703759.9 dated Aug. 1, 2017.
International Search Report and Written Opinion issued in International Patent Application No. PCT/GB2017/050634 dated Jul. 10, 2017.
Chinese Office Action received in Application No. 201780025596.8 dated Nov. 4, 2020.
Chinese Search Report received in Application No. 201780028596.8 dated Aug. 26, 2020, 13 pages.
Office Acton received in Japanese Application No. 2018-548113 dated Feb. 22, 2021, with translation, 11 pages.

* cited by examiner

DEVICE AND METHOD FOR HEATING OR COOLING A SAMPLE

CROSS-REFERENCE TO RELATED APPLICATION

This application is a 35 U.S.C. 371 National Phase of PCT Application No. PCT/GB2017/050634 filed Mar. 9, 2017 which claims priority to GB Application No. 1604062.8 filed Mar. 9, 2016. The disclosure of these prior applications are hereby incorporated by reference herein.

TECHNICAL FIELD OF THE INVENTION

The present invention relates to improvements in or relating to devices and/or methods for heating or cooling a sample and in particular, in relation to devices and/or methods for heating, thawing, cooling and/or freezing samples enclosed within bags or other containers.

BACKGROUND TO THE INVENTION

Samples are routinely stored within bags or other containers and are often chilled or frozen to preserve or improve shelf-life. Such chilled or frozen samples often need to be thawed or heated before use wherein it is usually desirable to carry out any thawing or heating in a safe and efficient manner. Further, in certain instances the maximum temperature of the sample may need to be kept below a certain value during and/or after heating/thawing, for example, where the samples comprise biological material or food products; whilst simultaneously ensuring that the sample is not contaminated in any way. In an exemplary case, where the frozen sample comprises biological material within a cryogenic bag or vial, it is vital that the sample is not contaminated in any way and usually that the temperature of the sample does not exceed 37° C., at which point the sample may be damaged irreparably.

Heating/thawing of samples may typically be carried out in a water bath where the sample bags or containers can be placed in water (or other fluids) which are generally kept at a temperature above the melting point of water. Using water (or other fluids) in this manner provides an effective means of ensuring the temperature does not exceed a chosen value. However, thawing samples in this manner raises issues in relation to the sterility of the water (or fluid) within which the bags/containers are submerged and sample contamination may therefore be an issue.

'Dry' systems for heating/thawing samples offer the advantages of sterility and safety when compared with water (or other fluid) based systems. However, it is characteristically difficult in a dry system to apply sufficient power to thaw samples without exceeding the maximum temperature to which samples should be heated. Furthermore, when freezing samples contained within a bag, the bag upon freezing, may flex. Dry systems of the art comprising a planar heating element will not provide a uniform heating profile across the bag when flex has occurred during freezing.

Similarly, there is a need to provide a means to cool or freeze samples in a safe and efficient manner. In certain instances this may involve ensuring that the temperature of the enclosed sample reduces at the same rate across the entire sample; whilst simultaneously ensuring that the sample is not contaminated in any way. In an exemplary case, where the sample comprises biological material within a cryogenic bag or vial, or comprises food products within a bag or flexible container, it is vital that the sample is not contaminated in any way and it would be advantageous to retain a constant temperature profile across the sample so as not to produce hot/cold spots when the sample is chilled or frozen.

Known chilling or freezing systems are typically constrained to 'dry' systems, such as those described above. However, as discussed, it is characteristically difficult to maintain a constant temperature profile across a sample using a dry system with planar heating/cooling elements, particularly when freezing samples within a flexible bag as the bag may flex during the process.

It is an aim of the invention to provide an improved device for heating or cooling a sample which overcomes or at least partially mitigates the problems associated with prior art devices. It is also an aim of the invention to provide an improved method for heating or cooling a sample which overcomes or at least partially mitigates the problems associated with prior art methods.

SUMMARY OF THE INVENTION

According to a first aspect of the present invention there is provided a device for heating or cooling one or more samples, the device comprising a plurality of members operable in use to heat and/or cool one or more samples, each of the plurality of members comprising a sample contact surface and a biasing means, wherein, in use: each member is biased, preferably resiliently biased, towards a resting position under the operation of said biasing means and is independently moveable with respect to each of the remaining members against said bias under the application of a force on the sample contact surface.

In this way, the device of the invention provides a means to provide a contact surface on a plurality of independently moveable members which conform to the shape of one or more samples contacting the members, or a bag or container within which samples to be heated or cooled are being stored. In this way, the device of the invention provides a 'dry' system which provides a uniform heating or cooling profile to address the problems associated with conventional dry systems.

When used throughout the specification, the terms "heat", "heated" and "heating" are intended to cover the application of heat energy to a sample. Particularly, reference to heating a sample may result in a temperature increase in a sample or a portion of a sample of at least 1, 2, 3, 5, 10, 20, 30, 40, 50, 100, 200, 250 or 275° C. The heated sample may be a solid sample e.g. a frozen sample or a sample which is partially frozen (e.g. which contains an ice fraction of at least 5, 10, 20, 30, 40, 50, 60, 70, 80 or 90%). The ice fraction is the amount or proportion of water in the sample which is present as ice rather than as liquid water. Alternatively, the sample may be a liquid or solution e.g. comprising biological material. The solid or liquid sample may be a cryopreserved sample which may comprise a cryoprotective additive (e.g. as dimethylsulphoxide, glycerol, ethylene glycol, sugars and polymers, singly or as mixtures).

Reference to "heating" includes the thawing of a sample. The term "thaw" or "thawing" as used herein refers to the process of converting ice to liquid water. The term "thawing" can alternatively be referred to as "melting". The thawing of a sample may occur at or before its melting temperature, with complete thawing occurring at the melting point. Thawing a sample thus refers to the conversion of any ice to water in the sample.

Any method known in the art to produce heat may be used to heat the sample in the present invention. Particular methods are discussed below.

Similarly, when used throughout the specification, the terms "cool", "cooled" and "cooling" are intended to cover the removal/conduction of heat energy from a sample. Particularly, reference to cooling a sample may result in a temperature decrease of the sample or a portion of the sample by at least 1, 2, 3, 5, 10, 20, 30, 40, 50, 100, 200, 250 or 275° C. Reference to "cooling" also includes the freezing of a sample, where "freezing" refers to a phase transition of liquid water to ice.

Particularly, an aqueous solution (e.g. comprising biological material) may be frozen, e.g. cryopreserved. For cryopreservation the aqueous solution may typically contain growth medium (salts, sugars etc.) together with a cryoprotective additive such as dimethylsulphoxide, glycerol, ethylene glycol, sugars and polymers, singly or as mixtures. The biological material may be in the form of a cell suspension, tissue or protein in solution. In foodstuffs the aqueous solution could contain, sugars, proteins, fats etc. During the initial freezing of an aqueous solution ice will form, removing water from the system. In the presence of a cryopreservant, the remainder of the system, including any cells present may be excluded from ice crystal formation and may become freeze concentrated into a residual unfrozen fraction. As the temperature is reduced more ice forms and the residual unfrozen fraction becomes increasingly concentrated until it solidifies at the glass transition temperature or eutectic temperature. At all temperatures between the initial freezing and the glass transition temperature a two phase system exists of crystalline ice and residual unfrozen fraction. Thus the device of the invention may be used to cryopreserve samples and this is included by reference to cooling a sample.

The temperature of the sample, container, or the members or a portion thereof can be measured or determined by using at least one temperature sensor or any other method well known in the art, as discussed further below. Thus an increase or decrease in temperature can be detected by measuring an initial temperature and a temperature after heat has been transferred to or from a member/sample.

The device may be operable in use to heat (e.g. thaw) one or more samples, (one or more solid or liquid samples), e.g. one or more frozen or chilled samples. Alternatively or additionally, the device may be operable in use to cool one or more samples. Thus, the device may be used as a freezing device for freezing one or more samples, or may be used to cryopreserve one or more samples. It is possible for a device to be capable of both heating and cooling a sample, where at least one portion of the members comprised within the device (e.g. of the plurality of members) are associated with heating and at least a different portion of the members comprised within the device are associated with cooling. For example, at least 10, 20, 30, 40, or 50% of the members of the device may be associated with or capable of heating a sample and/or at least 10, 20, 30, 40 or 50% of the members may be associated with or capable of cooling a sample. Alternatively, one or more of the plurality of members (e.g. at least 10, 20, 30, 40 or 50% of the members) may be capable of both heating and cooling a sample at different times, i.e. the heating and cooling function may be separated temporally.

As indicated above, the device is capable of heating and/or cooling at least one sample (one or more samples). The number of samples which can be heated and/or cooled by a device of the invention will be dependent on the size of the samples (and the containers in which the samples are comprised), the number of members, the contact surface area provided by the members present within a device and the percentage of members which are capable of heating and/or cooling. Generally, if the sample containers are smaller than the surface area provided by the plurality of members, then multiple samples may be heated and/or cooled simultaneously within a device of the invention. Particularly, it may be possible to heat or cool at least 1, 2, 3, 4, 5, 6, 7, 8, 9 or 10 samples simultaneously. As discussed further below, the temperature applied to each sample may be the same or different and may be varied over time or spatially across each individual sample.

Reference to a "plurality of members" as used herein refers to more than one and preferably to an array of members which are capable of either heating and/or cooling a sample when in use. The number of members within a plurality of members may depend on the size of and/or the number of sample containers that it is desired to heat or cool. However, particularly, at least 10, 50, 100, 200, 500, 1000, 2000, 3000, 5000, 7000, or 10000 members may be present.

A skilled person will appreciate that for the plurality of members to be capable of heating and/or cooling a sample in use, it is not necessary for all of the members to conduct heat to and/or away from a sample. Thus, it is possible that only a portion or group of the members of the plurality of members present in the device may be capable of conducting heat to and/or away from a sample. Particularly, at least 5, 10, 15, 20, 30, 40, 50, 60, 70, 80, 90 or 99% of the plurality of members may be capable of conducting heat to or from a sample (e.g. may be thermally connected to a heat source or a cooling element or coolant). Alternatively, it is possible that all of the plurality of members may be capable of conducting heat to and/or from a sample when in use. A heating member as referred to herein is a member which is capable of conducting heat to a sample in use (e.g. may be thermally connected to a heat source). A cooling member as referred to herein is a member which is capable of conducting heat away from a sample (e.g. may be thermally connected to a coolant or cooling element).

Further, a skilled person will appreciate that not all of the plurality of members may contact the one or more samples in use. Thus, particularly, at least a portion or group of the plurality of members may be in contact with the sample or sample container when in use, e.g. at least 5, 10, 20, 30, 40, 50, 60, 70, 80 or 90% of the plurality of members may be in contact with the sample.

Additionally, the device of the invention may comprise means for physically dividing the members into discrete subsets or groups. For example, the device of the invention may have other member-like structures, which may not comprise a biasing means. Such structures may be a similar or the same shape and/or size as one or more of the plurality of members. Further, typically the member-like structures may not be capable of heating or cooling the sample. Such member-like structures may allow the plurality of members to be separated into groups of members, e.g. which may allow discrete regions of the device to comprise groups of members which may be capable of differentially heating or cooling a sample, as discussed in detail below. The device of the invention may comprise one or more frame member(s) which can be configured to form a frame about a subset or group of heating/cooling members. The frame members could be dividing members which are movable between operative and inoperative positions. The dividing member(s) may located between the subset or group and the remainder of the heating/cooling members and be raised and lowered relative to the heating/cooling members for movement between operative and inoperative positions.

Thus, when the device is operable in use to heat one or more samples, one or more of the members is capable of heating the sample. Particularly, the one or more members may be operable in use to conduct heat energy from a heat source. More than one heat source may be used in this embodiment, e.g. more than 2, 3, 4, 5, 6, 7, 8 or 9 heat sources may be used. Each heat source may be capable of heating separate or discrete groups of members which may in turn heat discrete portions of a sample and/or different samples. In one aspect, one heat source may be used per member, i.e. for each member. Although in one particular embodiment of the invention, all members will be capable of conducting heat, it is also possible that only a portion or group of members have this capability.

Further, the device may be adapted to provide a thermal connection between one or more of the members and the heat source, in use, e.g. a material capable of conducting heat and/or an air gap. Particularly an air gap may be present between one or more members and the heat source (and/or cold source).

The device may comprise an integral heat source, or alternatively (or additionally) an external heat source may be used. The heat source (particularly an integral heat source) may comprise at least one heating element, e.g. at least 2, 3, 4, 5, 6, 7, 8 or 9 heating elements, where the at least one heating element may be thermally connected to at least one of the plurality of members, e.g. to a portion or group of the plurality of members. (A portion or group of the plurality of members as used herein may refer to at least 5, 10, 15, 20, 25, 30, 40, 50, 60, 70 or 80% of the plurality of members). In this way, the at least one heating element may conduct heat to said one or more members which may then heat the sample. Particularly, the at least one heating element may be thermally connected to all of the plurality of members. In this way heat may be conducted to all of the members, which may in turn heat a sample. In further embodiments a separate heating element may be provided within one or more of the plurality of members, e.g. within each member.

In some embodiments the heating element may comprise a ceramic material. However, in presently preferred embodiments the heating element may be formed from a metallic material. In such embodiments, the heating element may be formed from aluminium or silicon, for example, or may be an alloy of two or more different metallic elements.

In some embodiments the heating element may be connected to a power supply, such as the mains, for example. In such embodiments the heating element may be operable to increase in temperature when supplied with an electric current from the power supply. The power applied may be dependent on various factors e.g. the sample size to be heated (or cooled, where a cooling element is used as discussed below), the length of time for the heating to occur and/or the initial temperature of the sample and the desired temperature of the sample. For example at least a few Watts e.g. at least 1, 5 or 10 Watts may be used to heat a small sample in a few minutes, whereas at least 50, 100, 500, 1000, 2000, 2500 or 3000 Watts may be used for a larger sample. In some embodiments the heating element may heat up through resistive heating when an electrical current is passed there through, in use. Alternatively, heat may be generated by friction, microwave or RF (high frequency alternating electric field, microwave, radio wave etc.) or by exposure to an external heat source. The heating element may conduct its heat to at least one member of the plurality of members, as discussed above.

The one or more members may be alternatively heated by conduction of heat from a heat source such as a heated liquid or gas in contact with the one or more members and particularly isolated from the sample (i.e. to retain a dry system). In one embodiment, heated material (liquid or gas) may flow through, in or adjacent to said one or more members, (e.g. inside said one or more members (e.g. in one or more tubes). In this embodiment, said one or more members may comprise an inlet and an outlet for the heated material, to enable said heated material to enter and leave said one or more members.)

In embodiments wherein there is provided a thermal connection between one or more members and a heat source, the thermal connection may be direct. For example, the direct thermal connection may comprise a physical connection, such as a direct contact, of the one or more members and the heat source. The direct contact may comprise a direct contact of a conductive portion of the one or more members with the heat source. In such embodiments, heat energy may be transferred directly from the heat source to the one or more members through conduction. The heat source may be contained within each member or at least partially surround each member. Alternatively, the thermal connection between one or more members and a heat source may be indirect through an intermediary element. For example, in some embodiments the intermediary element may comprise a conductive material, operable in use to transfer heat energy from the heat source to one or more of the plurality of members. The intermediary element may directly contact both the heat source and one or more of the plurality of members.

In other embodiments, wherein the device is operable in use to cool one or more samples, the one or more members may be operable in use to conduct heat energy from one or more samples in order to reduce the temperature of said sample/s e.g. to at least one cold source which may comprise one or more cooling elements (e.g. more than 2, 3, 4 or 5 cooling elements). Particularly, the one or more members may be cooled by conduction of heat therefrom to a cold source such as a cooled material, e.g. a liquid or gas, or a solid, e.g. dry ice. The cooled material may be in contact with the one or more members, but may particularly be isolated from the sample e.g. from the outer surface of the members, to ensure and maintain a dry system. Thus, the cooled material may flow through, in or adjacent to one or more members, as discussed above in relation to heating. In this embodiment, the cooled material may comprise liquid nitrogen, carbon dioxide, or domestic or industrial refrigerants (e.g. when connected to a refrigeration engine), e.g. ammonia or various hydrocarbons such as propane.

The cold source may be integral to the device or may be external. The cold source may be a cooled liquid, solid or gas as previously described or may comprise a cooling element, such as a cooling element from a refrigerator (e.g. an evaporator plate), or from a Stirling engine (Cryocooler) or a Peltier cooler or device. In some embodiments the cold source may be thermally connected to at least one of the plurality of members or to a group or portion of the plurality of members, e.g. to each member. In such embodiments the cold source may be operable in use to conduct heat energy from the or each thermally connected member thereby reducing the temperature of the or each member, accordingly. In further embodiments there may be provided a separate cold source, e.g. cooling element within one or more (e.g. each) of the plurality of members.

In embodiments wherein there is provided a thermal connection between one or more members and a cold source, the thermal connection may be direct. For example, the direct thermal connection may comprise a physical connection, such as an abutment, of the one or more members and the cold source. The direct connection may comprise direct connection of a conductive portion of the one or more members with the cold source. In such embodiments, heat energy may be transferred directly from the one or more members to the cold source to the one or more members through conduction. The cold source may be contained within each member or may at least partially surround each member. Alternatively, the thermal connection between one or more members and a cold source may be indirect through an intermediary element. For example, in some embodiments the intermediary element may comprise a conductive material, operable in use to transfer heat energy from at least one of the plurality of members to the cold source.

One or more of the plurality of members may be operable in use to either heat or cool a sample as described herein.

As described above, in some embodiments the device comprises a heat source and/or a cold source (e.g. comprising a heating element and/or a cooling element). In some embodiments the heating and/or cooling element may comprise a planar surface. In alternative embodiments, the heating and/or cooling element may comprise a series of wells or cavities within which one or more of the plurality of members may move, in use. Particularly, the heating and/or cooling element comprises a series of wells or cavities, each well or cavity being operable in use to receive a single member, e.g. in a grid like structure.

In embodiments wherein the heating and/or cooling element comprises a series of wells or cavities within which one or more of the plurality of members may move, in use, the or each member may be only partially contained within a well or cavity. For example, in some embodiments only a portion of the or each member may be contained within a well or cavity. In some embodiments the portion of the member which is contained within the well or cavity is greater than or equal to the portion of the member which is outside the well or cavity. A skilled person will appreciate that when a greater portion of each member is present within the well or cavity, the more efficient the conduction of heat to or from the member will be. However, a portion of the member should be outside of the well or cavity in order to provide a surface upon which the sample can be placed. Thus, the ratio of the portion of the or each member contained within a well or cavity to the remainder of the same member, i.e. that is not contained within a well or cavity, may be from 1:1 to 100:1, e.g. from 2:1, 3:1, 4:1, 5:1, 6:1, 7:1, 8:1, 9:1, 10:1, 15:1, 20:1, 30:1, 40:1 or 50:1 to 60:1, 70:1, 80:1 or 90:1, for example. Alternatively viewed, at least 50, 60, 70, 80 or 85% of a member may be comprised within the well or cavity. A skilled person will appreciate however, that the ratio of the portion of the or each member contained within a well or cavity to the remainder of the same member may change, in use. For example, the ratio may change as the or each member moves against (or with) the bias provided by the biasing means.

Further, it will be appreciated, that members which have a greater or increased length (i.e. referring to the portion of the member which is parallel to the sides of the well or cavity, and not to the sample contact surface of the member), may have a greater surface area over which heat may be transferred to or from. Thus, it may be desirable in some circumstances to increase the length of the members. Typically, members may be at least 0.2, 0.5, 1, 2, 3, 4, 5, 6, 7, 8, 9, or 10 cm in length (when referring to the side of the member parallel to the well/cavity or alternatively viewed, the surface of the member which is perpendicular to the sample contact surface of the member).

In some embodiments the device may comprise a frame or outer casing within which at least a portion of one or more of the members is located, in use. In such embodiments, the or each member may be only partially contained within the frame or casing of the device, in use. For example, in some embodiments only a portion of the or each member may be contained within the frame or casing. In some embodiments the portion of the member which is contained within the frame or casing is greater than or equal to the portion of the member which is outside of the casing or frame. Thus, the ratio of the portion of the or each member contained within the frame or casing of the device to the remainder of the same member, i.e. that is not contained within the frame or casing of the device, may be 1:1, or may be 2:1, or may 3:1, or may be 4:1, or may be 5:1, or may be 6:1, for example. Alternatively viewed, at least 50, 60, 70, 80 or 85% of a member may be comprised within the frame or casing. Further, the ratio of the portion of the or each member contained within the frame or casing of the device to the remainder of the same member may change, in use. For example, the ratio may change as the or each member moves against (or with) the bias provided by the biasing means.

In a particular embodiment, the plurality of members are located on a supporting structure which itself is resiliently biased to a resting position and is moveable against said bias under the application of a force on the sample contact surface. The supporting structure may be a frame and/or may include a heating or cooling element in which the members are located. The supporting structure may be connected to one or more biasing means, e.g. one or more springs, which may typically be arranged on the opposing side or surface of the supporting structure to the plurality of members. The one or more biasing means, e.g. springs, may allow the supporting structure to be moved in response to the application of force (e.g. the presence of a sample/sample container on the plurality of members). This allows the device to compensate for a sample container which is more distorted than the plurality of members alone can compensate for. The biasing means attached to the supporting structure may thus allow gross adjustment of the device, whereas the plurality of members typically allow fine adjustment. As indicated above, the supporting structure may be attached to at least one biasing means, e.g. at least 2, 3, 4, 5, 6, 7, 8, 9 or 10 biasing means. As discussed in detail below, the biasing means may be formed from any material which biases the supporting structure towards a resting position and which allows the supporting structure to move against said one or more biasing means under the application of force, e.g. the application of a sample container onto at least one of the plurality of members. Particularly, the biasing means may be a spring, foam and/or a gas strut. The at least one biasing means attached to the supporting structure may be the same or a combination of different biasing means may be used.

In some embodiments the indirect thermal connection between one or more members and the heat source or cold source e.g. heating or cooling element, may comprise an air gap across which heat energy may be transferred between one or more of the plurality of members and the heat source or cold source (e.g. the cooled material or heating/cooling element). By providing an air gap the problems associated with conventional 'dry' systems relating to overheating (or overcooling) of samples can be controlled as the bag/container within which samples are stored are not directly in contact with the heat source or cold source (e.g. the cooled or heated material or heating/cooling element). Rather, the heat energy is transferred across the air gap providing greater control over the rate at which the energy is supplied to or removed from a sample. In some embodiments the biasing means is operable to maintain the air gap between the corresponding member and the heat source or cold source (e.g. the cooled or heated material or heating/cooling element).

In some embodiments the air gap may be no more than 0.05 mm, or may be no more than 0.1 mm, or may be no more than 0.2 mm, or may be no more than 0.3 mm, or may be no more than 0.5 mm. In some embodiments the air gap may be more than 0.5 mm. In presently preferred embodiments the air gap is less than 0.1 mm.

In some embodiments the plurality of members may be provided within a frame. The frame may be formed of a thermally conductive material, e.g. a metallic material, and may be in thermal contact with one or more of the plurality of members. In such embodiments, the frame may act as the intermediary element between the members and an external heat source, coolant or the heating/cooling element. It may be desirable to heat said one or more plurality of members using a heat pad attached to the frame which comprises said plurality of members. Particularly, the size of the heat pad may be minimised as far as possible to reduce the occurrence of a temperature gradient, whilst allowing said one or more of the plurality of members to be heated to a desirable temperature. Further, an increase in thickness of the frame upon which the heat pad is positioned can reduce or prevent the occurrence of a temperature gradient. In other embodiments the frame may act simply to retain the members in a certain configuration. In such embodiments, the thermal connection between the members and the external heat source, coolant or the integral heating/cooling element may be direct, or may be indirect through an additional intermediary element or air gap, as described above.

In embodiments wherein the device is operable to heat one or more samples, (e.g. when a sample is at a temperature below the ambient temperature of the environment in which the device is in use, or below a set temperature), a heat source may be operable to transfer heat energy to one or more of the plurality of members by means of radiation or convection of, or conduction through, gas molecules, or conduction through a conductive member between the heat source and the plurality of members as discussed above.

In embodiments wherein the device is operable to cool one or more samples, (e.g. when a sample is at a temperature above the ambient temperature of the environment in which the device is in use, or above a set temperature), heat energy from one or more samples may be transferred to one or more of the plurality of members by means of radiation or convection of, or conduction through, gas molecules, or conduction through a conductive member between one or more samples and the plurality of members.

As discussed above, each member of the plurality of members comprises a "sample contact surface". The sample contact surface is the portion of each member which is capable of being in contact with a sample or container comprising a sample in use. Thus, this is the portion of each member which is capable of directly touching or contacting a sample or container (e.g. comprising a sample), to be cooled or heated. Typically the sample contact surface will be found at the non-attached end of each member, i.e. the end which is not attached directly to another part of the device e.g. to a heat source and/or frame, and/or which is not contained within a well/cavity e.g. of the heating or cooling element (or is parallel thereto).

One or more of the plurality of members may comprise an elongate structure e.g. a substantially elongated structure. In such embodiments one or more of the plurality of members may comprise a pin, rod or bar, or may be any suitable hollow or solid tubular or cylindrical member. In such embodiments the sample contact surface of the one or more members may comprise a portion of an end of the elongate member, such as an end surface of the elongate member. The sample contact surface may protrude from the elongate member in one or more directions such that the cross-sectional surface area of the sample contact surface has a larger cross-sectional area than the elongate member.

In embodiments wherein the members comprise elongate members, the biasing means may be at least partially contained within the elongate member. In some embodiments the biasing means may be entirely contained within the elongate member. For example, the biasing means may comprise a spring or deformable resilient member within the elongate member. In other embodiments, the resilient member could be located below the elongate member, operative between the elongate member and a frame or other supporting structure. Where the elongate members are located in a well or cavity of a heating and/or cooling element, the resilient member may be operative between a base of the heating and/or cooling element and the elongate member. The resilient element in such an embodiment may be a compression spring.

In further embodiments one or more of the members may comprise a non-elongate member. In such embodiments the plurality of members may comprise a pad, key, button, plate or a disc, for example, which may be connected to a support structure such as a support arm or frame. The support arm may comprise an elongate pole or rod, for example, which may connect each of the non-elongate members to the device. The support arm may connect the non-elongate member to the biasing means, or a further supporting member or frame, for example. The support arm may comprise an articulated joint. The support arm may comprise integral biasing means, and in embodiments in which the support arm comprises an articulated joint, the articulated joint may comprise a biasing means, such as a spring, for example.

In embodiments wherein the members comprise non-elongate members, the biasing means may be at least partially contained within the non-elongate member. In other embodiments the biasing means may be entirely connected to at least a portion of the non-elongate member. For example, the biasing means may comprise a spring or deformable resilient member which is connected to a surface of the non-elongate member. In such embodiments the biasing means may also be connected to a portion of a support structure and may form the connection between the non-elongate member and the support structure.

In some embodiments one or more of the members may comprise an elongate member and a sample contact surface which may comprise a non-elongate member such as a pad, key, button, plate, disc or the like, for example.

Each member thus preferably comprises a sample contact surface which, in use, may contact a portion of one or more samples or a sample container to transfer heat energy to, or conduct heat energy from, a sample. In some embodiments the sample contact surface of at least one member may comprise a ceramic material. In some embodiments the sample contact surface of at least one member comprises a metallic material. In such embodiments, the sample contact surface may be formed from aluminium or silicon, for example, or may be an alloy of two or more different metallic elements. In presently preferred embodiments, the device comprises a heating and/or cooling element and the sample contact surface of one or more of the members comprises the same material as the heating and/or cooling element. Particularly, each complete member may comprise any of the materials listed above for the sample contact surface. It is possible however, for different members within the plurality of members to comprise different materials, e.g. from those described above.

In some embodiments the biasing means may be contained within its corresponding member within a volume which is defined by the sample contact surface. For example, the sample contact surface may entirely enclose the biasing means such that the biasing means is not visible, in use.

The sample contact surface of each member may have an area of up to 100 cm$^2$, e.g. up to 90, 80, 70, 60, 50, 40, 30, 20, 10, 5, 4, 3, 2, or 1 cm$^2$ or up to 5 mm$^2$ or 1 mm$^2$, e.g. less than 0.5, 0.4, 0.3, 0.2 or 0.1 mm$^2$. Particularly, in the present invention, the sample contact surface of the at least one member may range in diameter from e.g. 0.1 mm, 0.5 mm, 1 mm, 2 mm, 5 mm, 1 cm, 2 cm, 3 cm, 4 cm, 5 cm, 10 cm or more. Particularly, the members may be cuboid in shape and have a sample contact surface between 0.5-1.5 cm$^2$, particularly approximately 1 cm$^2$.

The sample contact surface of the member may be substantially flat or planar or may comprise a three-dimensional configuration. In embodiments wherein the sample contact surface is substantially flat, the surface may comprise any polygonal shape, which may be regular or irregular. For example, in some embodiments the sample contact surface may be circular, triangular, square, or rectangular, for example. In some embodiments the sample contact surface is substantially hexagonal. In embodiments wherein the sample contact surface comprises a three-dimensional configuration, the surface may, for example, comprise a substantially spherical, hemispherical, cuboidal or pyramidal configuration. In some embodiments the sample contact surface may be curved, concave or convex.

The sample contact surface of each of the members may comprise the same configuration. In other embodiments the sample contact surface of at least one member comprises a first configuration and the sample contact surface of one or more further members comprises a second configuration.

In some embodiments the device may be configured such that one or more samples or sample containers may contact only a portion of the plurality of members, in use. For example, in some embodiments the device may be configured such that one or more samples or sample containers may contact up to 10%, 20%, 25%, 30%, 35%, 40%, 45% 50%, 55%, 60%, 65%, 70% or 75% of the plurality of members. In some embodiments the device may be configured such that one or more sample or sample containers may contact each of the plurality of members, in use. The number of members in contact with one or more samples or sample containers, in use, will be dependent on the size and shape of the sample(s) or container. Each member may be moveable against said bias only under the application of a force upon the sample contact surface. Therefore, in embodiments wherein, in use, one or more sample or sample containers contacts only a portion of the plurality of members, only those members in contact with the sample(s) or container will be moved against said bias, whilst any remaining members will be retained in the resting position under the bias.

The plurality of members may be provided in one or more groups. In embodiments wherein there is provided a single group of members, the members may be arranged in a matrix covering a given area, which may comprise at least two members in one or two directions, such as a 2×1, 3×1, 2×2, 3×3 or 4×4 matrix, for example. In some embodiments there may be at least 5 members, or at least 10 members, or at least 20 members in one or both directions. As discussed above, it is possible for groups of members to be separated from each other by member-like structures, dividing members or other means, where the member-like structures or dividing means may not comprise a biasing means.

In some embodiments the plurality of members may be provided in a plane. In such embodiments one or more, and preferably each of the plurality of members may be aligned perpendicular to the plane. In some embodiments the plurality of members may be provided in a single horizontal plane onto which a sample may be placed, in use, with one or more of the plurality of members being aligned vertically. In such embodiments, each member may be operable to move along a vertical axis against its bias under the weight of a sample. In embodiments wherein the plurality of members are provided in a single horizontal plane, one or more sample or sample containers may be orientated horizontally when placed on to one or more of the plurality of members.

In further embodiments the plurality of members may be provided in a single vertical plane against which a sample may be placed in an abutting relationship, in use, with one or more of the plurality of members, and preferably each of the members being aligned horizontally, perpendicular to the plane. In such embodiments, each member may be operable to move along a horizontal axis against its bias under the force provided by abutment of one or more sample of sample container with the plurality of members. In embodiments wherein the plurality of members are provided in a single vertical plane, one or more sample or sample containers may be orientated vertically when placed against one or more of the plurality of members.

In some embodiments the device comprises two or more planes of members which may be configured as set out above with one or more of the plurality of members being aligned perpendicular to the plane/s. In some embodiments each plane comprises a separate group of members and one or more members from each group is aligned perpendicular to its corresponding plane.

There may be provided two substantially horizontal planes of members. In such embodiments there may be provided a first horizontal plane onto which a sample may be placed and a second horizontal plane which itself may be placed onto an opposing surface of a sample, in use. In this way, the device of the invention provides a means to heat or cool two opposing surfaces of a sample. In further embodiments there may be provided two substantially vertical planes of members. In such embodiments there may be provided a first vertical plane and a second vertical plane between which a sample may be placed, in use. Again, this configuration provides a means to heat or cool two opposing surfaces of a sample but in a different orientation. The orientation of the planes/groups of members may be chosen dependent on the need to keep a sample or samples in a given orientation during the heating or cooling process.

In some embodiments the device may comprise two or more groups or planes of members which may be moveable between two or more configurations such that the device may be used to heat or cool a sample or samples in two or more different orientations, in use. For example, in embodiments wherein the device comprises two planes of members, the two planes may be moveable between a horizontal orientation and a vertical orientation as is required.

In some embodiments two or more of the plurality of members may be arranged to form one or more substantially tubular recesses into which one or more samples or sample containers may be placed, in use, with the sample contact surfaces of two or more members defining the walls/surfaces of the or each recess. For example, in some embodiments two or more of the plurality of members may be arranged to form a substantially cylindrical recess into which a container, which may be a vial or other cylindrical container, may be placed. In other embodiments the recess may comprise a substantially triangular, square, rectangular or other polygonal-shaped cross-section, which may or may not be complimentary to the shape and configuration of a sample or sample container.

The device may comprise a means to apply an additional force to a sample or samples when positioned on the device, in use. The device may be operable to apply the additional force to a surface of the sample/s. The surface may be an opposing surface of the sample/s to the surface/s in contact with one or more of the plurality of members. In such embodiments, the device may be operable to apply a force to the surface of the sample/s, the force acting to push the sample/s against one or more members to move said member/s against their bias. This additional force may be required when using the device of the invention in instances wherein the weight of the sample or samples is not great enough to sufficiently move one or more of the plurality of members against the bias provided by the biasing means or when it is desired to urge a sample having an irregular shape into a regular shape during heating and/or cooling, for example. The additional force applied, or required to be applied, may be dependent on the sample/s to be heated or cooled, and/or the strength of the bias provided by the biasing means. In some embodiments the additional means may be operable to apply a force of up to 1 N, or may be at least 1 N, 2.5 N, 5 N, 7.5 N, 10 N, 15 N, 20 N, 25 N, 30 N, 40 N, 50 N, 75 N, 100 N, or 150 N, for example.

The means to apply an additional force may comprise a plate which may have a substantially flat surface thereon. The substantially flat surface of the plate may be operable to be placed into contact with the sample/s on the device, in use, to apply an additional force thereto. In embodiments wherein the plurality of members are position within a horizontal plane, the plate may be operable in use to be placed onto an upper surface of the sample/s to provide a downwardly directed force. The downwardly directed force may be provided by the weight of the plate itself. In such embodiments, the plate may weigh up to 0.1 kg, or may be at least 0.25 kg, 0.5 kg, 0.75 kg, 1 kg, 1.5 kg, 2 kg, 2.5 kg, 3 kg, 4 kg, 5 kg, 7.5 kg, 10 kg, or 15 kg, for example.

In some embodiments the device may comprise a lid or cover. The lid or cover may be moveable to a position whereby it covers one or more of the plurality of members, or one or more groups of members, or one or more planes of members. In some embodiments the lid or cover may be moveable to a position whereby it covers each of the members of the device. In some embodiments, the lid or cover may be operable in use to contact a surface of a sample or samples placed onto or against one or more of the plurality of members, and thereby may comprise the means to apply an additional force to the sample/s. The surface of the sample or samples contacted by the lid or cover, in use, may be an opposing surface of the sample/s to the surface/s in contact with one or more of the plurality of members.

The lid or cover may be moveable between a position whereby it covers one or more of the plurality of members, or one or more groups of members, or one or more planes of members, to a position whereby one or more of the plurality of members is uncovered. In some embodiments the device may comprise a lid or cover which is hingedly connected thereto, wherein the lid or cover is moveable with respect to the rest of the device, and in particular with respect to one or more of the plurality of members, through rotation about the hinged connection.

The lid or cover may comprise the means to apply an additional force to the sample or samples, as described hereinabove. The means to apply an additional force to the sample or samples and/or the lid or cover may comprise, or be connected to one or more heating and/or cooling members as described above, and may comprise or be connected to a plane of members.

Alternatively viewed, the means to apply an additional force to the sample may further be capable of heating or cooling the sample. Thus, the means to apply an additional force to the sample may comprise at least one heat or cooling source (e.g. at least one heating or cooling element) as previously discussed. In one embodiment, the means to apply an additional force may comprise at least three heating or cooling elements, which may be evenly spaced across or along the means, e.g. one heating element may be at the top of the means, one heating element may be in the middle of the means and one may be at bottom of the means. It may be possible to differentially heat or cool the at least one heating or cooling element, e.g. to heat or cool a particular element depending on the location of the sample within the device (on the plurality of members).

The apparatus may comprise a closing mechanism for positively holding the lid or cover in a closed position, i.e. preventing the uncovering of the said at least one of the plurality of members. This could be a lock such as a mechanical clasp which may clamp the lid or cover in the closed position. Alternatively, or in addition, the closing mechanism may apply a force to bias the lid or cover to the closed position. The closing mechanism could include one or more springs for applying a closing force to the lid or cover. The spring or springs could be of any suitable type and could be mechanical, such as one or more torsion springs, or gas/fluid or a combination. For example, the closing mechanism could include one or more gas or hydraulic struts which apply a closing force to the lid or cover. The closing mechanism may therefore allow a positive downwards force to be applied to said one or more plurality of members (and any sample containers positioned thereon). In a particular embodiment, the closing mechanism may include means to release the lid or cover once the sample has reached a desired temperature.

In some embodiments the device may be operable in use to control the operation of at least one of the plurality of members, or at least one group of members independently from each of the other members or groups of members. For example, in embodiments wherein the members are capable of heating, the device may be operable in use to independently control the heat energy transferred to each member, or group of members, via the one or more heat sources/heating elements.

In embodiments wherein the members are capable of cooling, the temperature of one or more of the members, or groups of members, may be controlled independently to control the extent to which the heat energy within a section or sections of a sample or samples is transferred to the members. For example, where a section or sections of a sample or samples is to be cooled more quickly than another section/s, the temperature of the corresponding member or members in contact with the first section or sections may be reduced with respect to each of the remaining members or groups of members.

In this way, the device provides a means to spatially differentially heat or cool a sample or samples by providing a means to choose the section or sections of a sample or samples which are heated/cooled, in use, wherein the section or sections may be separated from one another. This is particularly advantageous in embodiments wherein a sample or samples are dimensioned such that only a portion of the members are in contact with a sample during the heating or cooling process. In such embodiments, the device allows a user to choose to heat/cool only those members or groups of members which are in contact with a sample or samples.

In embodiments wherein the device comprises two or more groups of members, each group of members may be operable to be heated/cooled to the same level or differentially. For example, in embodiments wherein the members are arranged in two or more planes, each plane may be heated/cooled to the same temperature or to a different temperature. In this way, the device of the invention provides a means to heat/cool various regions of a single sample differentially, or indeed each of a plurality of different samples differentially.

In further embodiments each of the members or groups of members within a plane may be able to be heated/cooled differentially, in use. In this way, the device provides a means to vary the heating/cooling profile across the plane. This is particularly advantageous, for example, in embodiments wherein the device comprises one or more vertical planes, a sample or samples may move to a given end of the container within which they are contained, in use. In such embodiments it may only be necessary to heat/cool the portion of the container within which a sample/samples are contained.

In further embodiments the device may be operable in use to temporally differentially heat or cool a sample or samples. For example, in embodiments wherein the members are capable of heating a sample, the device may be operable in use to independently control when and to what extent heat energy is transferred to each member, or group of members, via the one or more heat sources/heating elements. In this way, the device provides a means to heat different sections of a sample or samples at different times. In embodiments wherein the members are capable of cooling a sample, the temperature of one or more of the members, or groups of members, may be controlled independently to control when and to what extent heat energy within a section or sections of a sample or samples is transferred to the members. For example, the temperature of one or more of the members or groups of members may be varied over time to temporally vary the extent to which heat energy within a section or sections of a sample or samples is transferred to said members.

In some embodiments, the extent to which at least 1, or at least 2, or at least 3, or at least 4, or at least 5, or at least 6, or at least 7, or at least 8, or at least 9 or at least 10 discrete regions of a sample may be heated or cooled may be chosen independently. In some embodiments the extent to which the at least 1, 2, 3, 4, 5, 6, 7, 8, 9 or 10 discrete regions of a sample may be heated or cooled may additionally or alternatively be operable to be temporally varied, the temporal variation of the heating or cooling of each discrete region being independent of the remaining regions.

In some embodiments the device may comprise a means to agitate a sample or samples, in use, during the heating or cooling process. Such embodiments are particularly advantageous where the device is used as a heating device.

In some embodiments the device may be operable to agitate a sample or samples through vibration, shaking, stirring, rotating, rolling, squeezing, displacing, prodding, or flexing, for example. The device may be operable to perform the agitation at a particular frequency and/or amplitude, (e.g. from 0.1 to 10 mm for lateral motion, and from 0 to 4000 rpm for orbital motion for vials). The device may be operable to agitate a sample for a particular time period e.g. from at least 1, 2, 3, 4, 5, 10, 20, 30, 40, or 50 seconds to at least 1, 2, 3, 4, 5, 6, 7, 8, 9 or 10 minutes. In use, the particular agitation type chosen will depend on the type of sample which is initially provided, i.e. on the ice fraction in a sample and on the container type/volume and/or the volume of sample material. The agitation type may also be dependent on the thermal conductivity of the members and/or sample. Alternatively or additionally, the container, e.g. its volume and geometry will dictate the required agitation. In particularly, in embodiments wherein the sample container is a vial or tube, orbital agitation may be adopted, whereas in embodiments wherein the container is a bag, squeezing, displacing, prodding and/or flexing may be adopted.

In some embodiments at least one of the plurality of members may be operable in use to agitate a sample or samples. In embodiments wherein the device comprises one or more groups of members, at least one group of members may be operable in use to agitate a sample or samples. In embodiments wherein the device comprises one or more planes of members, at least one plane of members may be operable in use to agitate a sample or samples.

In some embodiments, one or more of the plurality of members may be operable in use to vibrate in order to agitate the sample or samples. In further embodiments one or more of the plurality of members may be operable in use to oscillate between two or more positions in order to agitate a sample or samples. In some embodiments one or more of the plurality of members may comprise an agitation means. In such embodiments the agitation means may be operable in use to cause the corresponding member or members to vibrate or oscillate in order to agitate a sample or samples.

In an embodiment, the agitation means may be a spring relieved agitator, wherein said spring relieved agitator is capable of applying force to a sample but may reduce the force or yield depending on, say, the ice fraction present within a sample. Typically, when a frozen sample is present, a spring relieved agitator may not agitate said sample. This may be advantageous if a sample is provided in a container such as a bag, which may be damaged by agitation in a frozen state. In a particular embodiment, said agitator may be a force-limited oscillating agitator.

In some embodiments, each of the plurality of members may be operable to agitate a sample or samples independently of each of the other of the plurality of members. In this way, the device provides a means to spatially differentially agitate a sample or samples by controlling which of the members is used to agitate a sample or samples, in use. Thus, each member may be provided with an agitation means which can ensure that each member can independently agitate a sample in use. It will be appreciated that not all of the members may comprise an agitation means, but particularly, at least 10, 20, 30, 40, 50, 60, 70, 80 or 90% of the members may comprise an agitation means or may be attached to an agitation means, allowing their agitation, particularly allowing independent agitation of each member or of a group of members. Hence, the device may comprise at least one agitation means, e.g. at least 2, 3, 4, 5, 10, 20, 30, 40, 50 or 100 agitation means.

In further embodiments the device may be operable in use to temporally control the agitation provided by one or more of the plurality of members capable of heating. For example, one or more of the plurality of heating members may be operable to intermittently agitate a sample or samples, for example at least, every 30, or every 25, or every 20, or every 15, or every 10, or every 5, or every 4, or every 3, or every 2, or every 1 seconds, for example. The time between agitation events may be constant or may vary. In further embodiments the heating member/s capable of heating may be operable to vary the agitation provided over time in response to one or more factors. For example, in some embodiments, one or more of the plurality of members capable of heating may be operable to vary the interval between each change in agitation depending on the physical characteristics of a sample. For example, in embodiments wherein the device comprises a plurality of heating members (for heating a sample) the agitation may be changed when a particular ice fraction is present in a sample, e.g. when a sample is less than 99, 95, 90, 85, 80, 75, 70, 65, 60, 55, 50, 45, 40, 35, 30, 25, 20, 15, 10 or 5% ice in volume, or particularly, wherein less than 99, 95, 90, 85, 80, 75, 70, 65, 60, 55, 50, 45, 40, 35, 30, 25, 20, 15, 10 or 5% of the water in a sample is ice.

The device may additionally comprise one or more sensors. The one or more sensors may be operable in use to monitor one or more characteristics of the members, and/or a sample, and/or the container within which a sample is contained, and/or the environment within the device. In some embodiments the device may be operable in use to adjust the heating/cooling profile and/or the agitation provided in response to the monitored characteristics.

In some embodiments the one or more sensors may comprise temperature sensors which may be operable in use to monitor the temperature of one or more of the members. In some embodiments the one or more temperature sensors may be operable in use to monitor the temperature of a sample, or at least one or more regions within a sample. In further embodiments the one or more temperature sensors may be operable in use to monitor the temperature of the container within which a sample is contained, or at least one or more regions within the container. For example, in some embodiments the one or more temperature sensors may be operable in use to monitor the temperature of at least a portion of a wall of the container, which may be an interior or exterior wall. The one or more temperature sensors may comprise infra-red emission sensors operable in use to detect infra-red emissions from one or more areas of the device and/or a sample and/or the container, the infra-red emissions being indicative of the temperature of the relevant component. By way of an example, in embodiments wherein the device is used as a heating/thawing device, the one or more temperature sensors may be operable in use to monitor the changes in the temperature of a sample or container as a sample thaws/heats. In response, the device may be operable to vary the heating profile and/or agitation provided by, for example, increasing the heating effect or agitation at areas which are determined to have a low temperature (with respect to the target temperature to which a sample is to be heated), or conversely decreasing the heating effect or agitation at areas which are determined to have a temperature closer to the target temperature to which a sample is to be heated, i.e. at those areas which have thawed quickest. In such embodiments the device may be operable in use to cease the heating and/or agitation effects of one or more of the members at the point where a sample (or specific regions within a sample) are determined to have reached the target temperature.

In a particular embodiment, the device may contain at least 2, 3, 4, 5, 6, 7 or more sensors (e.g. temperature sensors, particularly IR sensors). The at least one sensor may be placed anywhere in the device, but in a particular embodiment, may be placed on a lid or cover which may be comprised within the device (e.g. a lid or cover may be present particularly where the plurality of members are provided on a horizontal plane). Alternatively and/or additionally, the at least one sensor may be placed underneath the plurality of members.

In further embodiments the one or more sensors may comprise structural sensors. In some embodiments the one or more structural sensors may be operable in use to determine the ice fraction of a sample. For example, in embodiments wherein the device is used as a heating/thawing device, the one or more structural sensors may be operable in use to monitor the changes in the ice fraction of a sample as it thaws/heats. In response, the device may be operable to vary the heating profile and/or agitation provided by, for example, increasing the heating effect or agitation at areas which have a high ice fraction, or conversely decreasing the heating effect or agitation at areas which have a low ice fraction, i.e. at those areas which have thawed quickest. For example, the agitation may be changed when a particular ice fraction is determined to be present in a sample, e.g. when a sample is less than 99, 95, 90, 85, 80, 75, 70, 65, 60, 55, 50, 45, 40, 35, 30, 25, 20, 15, 10 or 5% ice in volume, or particularly, wherein less than 99, 95, 90, 85, 80, 75, 70, 65, 60, 55, 50, 45, 40, 35, 30, 25, 20, 15, 10 or 5% of the water in a sample is ice.

In one aspect, the one or more sensors may allow post-heat or cooling imaging of a sample, e.g. immediately prior to removal of the sample from the device.

In some embodiments the device comprises two or more different types of sensor. For example, the device may comprise one or more temperature sensors and one or more structural sensors.

Each of the plurality of members comprises a biasing means. The biasing means may comprise a resilient material (or alternatively viewed, an elastic or flexible material), such as a resilient material which is resiliently deformable under the application of a force. The term "resilient" as used herein refers to the ability to be able to recoil or spring back into shape after the application of a force (e.g. after being compressed, stretched or bent) e.g. particularly into substantially the same shape, as before the application of a force. Particularly, the biasing means may comprise a material that applies an opposite force or resistance in order to be displaced or deformed. The biasing means may therefore comprise a spring, e.g. a compression spring, or foam, an elastic material, rubber or silicone. Typically, the biasing means may comprise a coil spring.

The plurality of members are resiliently biased towards a resting position as discussed above. This refers to the position of the members, prior to any force being applied. This position may be determined by the biasing means used within each member and the material comprised within the biasing means e.g. a spring. Since the biasing means generally comprise a material which is capable of being compressed under the application of a force and which is capable of returning to its original shape (or substantially its original shape) after removal of the force, the biasing means will determine the resting position of the member within which it is comprised, which will correspond to the resting position of the resilient (or alternatively viewed elastic) material within the biasing means of each member.

The plurality of members comprised within the device are independently movable as discussed above. Thus, each member may move independently to every other member (i.e. the movement of one or each member does not influence or impact on the movement of another or each other member). Particularly, when a sample or container is placed on the sample contact surface of the plurality of members, this provides a force, which may result in the independent movement of one or more of the plurality of members. Thus, the application of a force particularly refers to the placement of a sample or container comprising a sample on to the sample contact surface.

In some embodiments at least one of the plurality of members may additionally comprise a supporting member which may be operable in use to control the extent to which the corresponding member may be moved against the bias provided by the biasing means. In this way, the supporting member may be operable in use to ensure that an air gap is retained between each member and an integral heating or cooling element or external heat/coolant source at all times, in use.

In use, the device may be operable to heat or cool a sample or samples contained within a container. The "container" as used herein may be any container in which a sample may be placed. Typically the container will be a container in which a sample can be placed to freeze a sample, and thus typically the container will be able to exist at low temperatures, e.g. at temperatures of at or below −196° C. (the temperature of liquid nitrogen). A container may be a tube, vial, plate, straw or any other known container which can comprise a sample. Particularly, the container may be a screw capped cryovial, a hermetically sealed cryovial, a flexible bag, a multiwall plate, a matrix tube or a straw. The container may be able to hold any volume of sample and the present devices of the invention can be employed regardless of the volume of the container. A skilled person will appreciate that a device can be manufactured to heat or cool any container size. However, in a particular embodiment of the invention, the container may have a capacity of at least 50 µl, 100 µl, 0.2 ml, 0.3 ml, 0.4 ml, 0.5 ml, 1 ml, 2 ml, 5 ml, 10 ml, 50 ml, 100 ml, 500 ml or 1000 ml. Further, as indicated above, the container may be made of any material, although preferably from a material that can exist at low temperatures (e.g. at −196° C.). The walls of the container may be of any thickness, e.g. from 0.5 mm, 1 mm, 2 mm, 3 mm or 4 mm in thickness. Particularly, when the container is a bag, the wall thickness may be less than 0.5 mm, e.g. less than 400, 300, 200, 100, 50, 40, 30, or 20 µm.

The container may comprise any volume of sample and may or may not be filled to its capacity with sample. The container may therefore only be partially full. In this instance, a sample may comprise at least 1, 5, 10, 15, 20, 25, 30, 35, 40, 45, 50, 55, 60, 65, 70, 75, 80, 85, 90, 95 or 100% of the volume of the container.

The configuration of the independently moveable members is such that they conform to the shape of the container, which may be irregular. For example, in embodiments wherein the device is used to heat or thaw a frozen sample or samples contained within a flexible container, the container may be irregular due to flexing of the flexible container during freezing of a sample.

The device may be operable in use to heat or cool any type of sample. In presently preferred embodiments the device may be operable to heat or cool a sample which is required to remain uncontaminated.

The term "sample" as used herein refers to any sample type and particularly includes a sample comprising biological material, e.g. a cellular sample. The sample may comprise material such as a biopharmaceutical; cellular material; biological tissue; biological organ or part thereof; a nucleic acid; or a polypeptide or amino acid, for example.

In some embodiments the sample may comprise a food product or a drink or beverage product which may include food supplements or nutritional products, e.g. a packaged food product or a packaged drink or beverage product. For example, the food product may be meat/s, seafood, bread, vegetables, fruit, dairy products, cereals, sauces, condiments, dough, extracts, essences, nutraceuticals, vitamin or mineral supplements, herbal or botanical extracts or any combination thereof. In use, the device of the invention may be operable to heat such food items, thaw such food items which have been frozen previously, cool such food items and/or freeze such food items.

The sample may further comprise a cryoprotectant, which is a substance used to protect biological material from freezing damage (e.g. due to ice crystal formation). Cryoprotectants generally function by increasing the solute concentration in cells and preferably are not toxic to cells (or have minimal toxicity). Cryoprotectants may lower or reduce the glass transition temperature of a biological material within a sample and may allow vitrification of a material without ice crystal formation. Cryoprotectants may also displace water molecules forming hydrogen bonds with biological molecules and thus may replace the water molecules in the biological material. The sample used herein may comprise a mixture of cryoprotectants i.e. more than one cryoprotectant. Typical cryoprotectants include glycols e.g. ethylene glycol, propylene glycol and glycerol, and dimethylsuphoxide (DMSO), sugars e.g. trehalose, sucrose, and as indicated above, these can be used in isolation (i.e. singly) or in combination. Generally, if a sample comprises a cryoprotectant, between 1-30% of the sample may be cryoprotectant, e.g. between 1-20% or 5-15%.

The sample as described herein may be "frozen" and the device may be operable to thaw the sample/s, e.g. in a method of the invention. A "frozen" sample generally refers to a sample where at least 10, 20, 30, 40, 50, 60, 70, 80, 90 or 100% of the water in the sample is in the form of ice. Alternatively viewed, a frozen sample may contain no liquid water, or less than 90, 80, 70, 60, 50, 40, 30, 20, 10 or 5% of the water is liquid water. Thus, in a frozen sample, some non-frozen material (liquid water) may be present (and thus a frozen sample includes a partially frozen sample), but typically, the non-frozen material or liquid water is less than 90, 80, 70, 60, 50, 40, 30, 20, 10 or 5% of the sample volume.

In embodiments wherein the sample comprises a cryopreserved sample, the sample may have an initial temperature of no more than −100° C., −90° C., −80° C., −70° C., −60° C., −50° C. or 40° C., for example. Such a sample may be heated or thawed using a device or a method of the invention. In other embodiments, the temperature of a sample may be reduced to at least −200° C., or at least −175° C., or at least −150° C., or at least −125° C., or at least −100° C., or at least −90° C., or at least −80° C., or at least −70° C., or at least −60° C., or at least −50° C. or at least −40° C., for example by a device or method of the invention. The exact cryotemperature required will depend on the sample material and cryoprotectant used, as well as intended storage periods.

The members as described herein may be operable to heat a sample, or sample container to an ambient temperature, or to at least 20° C., 25° C., 30° C., 31° C., 32° C., 33° C., 34° C., 35° C., 36° C., 37° C., 38° C., 39° C., 40° C., 50° C., 60° C., or 70° C., for example. In embodiments wherein the sample comprises a biological material it may be desirable to heat the sample to a maximum of 37° C., above which cells within the material may become damaged. Alternatively viewed, at least one of the plurality of members may be heated to at least 20° C., 25° C., 30° C., 31° C., 32° C., 33° C., 34° C., 35° C., 36° C., 37° C., 38° C., 39° C., 40° C., 50° C., 60° C., or 70° C. Thus, in one aspect, at least one of the plurality of members may be heated to a temperature above that at which the sample is desired to be heated. Particularly, for a biological sample, for which it may not be desirable to heat above 37° C., the members may be heated to at least 70, 60, 50 or 40° C. when the sample is frozen and the temperature of the members may be reduced as the sample thaws, e.g. as a function of the remaining ice fraction. Alternatively (or additionally), the at least one member in contact with the sample may be mechanically moved away from the sample (i.e. to remove contact between the at least one member and the sample), as the thaw progresses or when the desired sample temperature is reached. A further alternative allows the sample or sample container to be moved away from the at least one member in contact therewith as the thaw progresses or when the desired sample temperature is reached.

Alternatively viewed, where a sample is to be thawed, the members may be operable to heat a sample, or sample container to at least 0° C., 1° C., 2° C., 3° C., 4° C., 5° C., 10° C., 15° C., or ambient temperature, for example.

In further embodiments the members may be operable in use to initially heat or cool a sample, or sample container to a given temperature, and then retain a sample or sample container at that temperature for a given length of time.

In some embodiments the device may additionally comprise a flexible membrane. The flexible membrane may be positioned over at least a portion of the sample contact surface of one or more of the plurality of members. In some embodiments the flexible membrane may be positioned over each of the plurality of members. However, it will be appreciated that the size of the flexible membrane may be selected based on the sample (container) size and the area of the plurality of members which would be in contact with the sample. In such embodiments, the flexible membrane may be positioned between one or more samples or sample containers and one or more of the plurality of members. In some embodiments the flexible membrane may be moulded about the sample contact surface of one or more of the plurality of members. In presently preferred embodiments the flexible membrane may comprise a thermally conductive material, which may be silicone, latex rubber, polyurethane, polyethylene, methacrylate-based resins, EVA for example. The flexible membrane may be operable in use to prevent any contaminants or portions of one or more samples or sample container from falling or moving between any spaces between adjacent members.

The flexible membrane may have a thickness of at least 20 µm, 30 µm, 40 µm, 50 µm, 75 µm, 100 µm, 250 µm, 500 µm, 1 mm, 2 mm, 3 mm, for example. The thickness of the flexible membrane may be substantially equal across the entire membrane. In other embodiments the thickness of the membrane may vary at certain points or regions of the membrane.

In a particular embodiment, the device may comprise at least one imaging system to allow sample identification and/or post heat/cool imaging of a sample prior to removal. Thus, the device may comprise at least 1, 2, 3, 4, 5 or more imaging systems. The imaging system may be placed at any suitable location within or on the device and particularly may be placed within or on the lid or cover of the device, particularly on the surface of the lid or cover which in use will be adjacent to the plurality of members. The imaging system may comprise at least one barcode scanner, and/or camera. Thus, a single imaging system may comprise a barcode scanner and camera, or a selection of these components. A skilled person will appreciate that if multiple imaging systems are present within the device, each imaging system may be the same (e.g. may comprise the same components) or different (e.g. may comprise different combinations of components). A barcode scanner may allow an imaging system as defined herein to detect the presence of a barcode which is positioned in front of the scanner, e.g. a barcode on a sample container and/or on a flexible membrane. Such barcode readers are available commercially (e.g. from Adafruit). Further, it is possible that a barcode reader may additionally be modified or controlled to be capable of taking a photographic image (i.e. to act as a camera), e.g. by controlling the imaging sensor. It may be desirable to obtain a photographic image of a sample after the application of heat or cooling in a device of the invention, to provide a record of the treatment.

A device in accordance with the invention may comprise at least one RFID module. A RFID module may be capable of detecting the presence of a RFID tag on a sample container and/or on a flexible membrane.

According to a second aspect of the invention there is provided a method of heating or cooling a sample comprised within a container, the method comprising contacting said container with one or more of a plurality of members, wherein said one or more of the plurality of members in contact with said container either provides a source of heat energy to the container to heat the sample contained therein or conducts heat energy from the container to cool the sample contained therein, wherein each of the plurality of members are biased towards a resting position and are independently moveable with respect to one another against said bias to a position.

The method of the second aspect of the present invention may be performed using a device in accordance with the first aspect of the present invention. The device may comprise any or all of the features of the first aspect of the present invention as is desired or appropriate.

In some embodiments the method may comprise thawing a frozen sample as previously defined contained within a container. In other embodiments the method may comprise freezing a sample contained within a container. In such embodiments, the method may comprise cryopreserving a sample contained within said container.

The method may comprise heating or cooling a sample comprising biological material, e.g. a cellular sample, as previously defined.

The method may comprise heating or cooling the sample to a different temperature to the container within which the sample is contained. For example, the method may comprise heating an external wall of the container to a first temperature whilst keeping the temperature inside the container at a second, lower temperature. Alternatively, the method may comprise cooling an external wall of the container to a first temperature whilst keeping the temperature inside the container at a second, higher temperature.

For heating or thawing a biological sample, the method may comprise heating an external wall of the container to a temperature above 37° C., which may be at least 40° C., 50° C., 60° C., or 70° C., for example, whilst keeping the internal wall temperatures at or below 37° C. In this way the method may allow a sample to thaw or heat more quickly due to the increased heat energy being supplied to the sample, whilst simultaneously ensuring that the sample remains at a safe temperature (e.g. less than or equal to 37° C.) above which it may become irreparably damaged.

The method may additionally comprise monitoring one or more characteristics of the members, and/or the sample, and/or the container within which the sample is contained, e.g. temperature (particularly using one or more temperature sensors). In some embodiments method may comprise adjusting the heating/cooling profile and/or the agitation provided in response to the monitored characteristics.

The characteristic/s of the temperature control members, and/or the sample, and/or the container within which the sample is contained may be monitored using one or more sensors. The one or more sensors may comprise one or more temperature sensors and the method may comprise using the one or more temperature sensors to monitor the temperature of one or more of the members, and/or the sample, or at least one or more regions within the sample, and/or the temperature of the container within which the sample is contained, or at least one or more regions within the container. For example, in some embodiments the method may comprise using one or more temperature sensors to monitor the temperature of at least a portion of a wall of the container, which may be an interior or exterior wall. The method may comprise monitoring the temperature of both the sample and the container. In some embodiments the method may additionally comprise varying the heating profile and/or agitation provided by, for example, increasing the heating effect or agitation at areas which are determined to have a low temperature (with respect to the target temperature to which the sample is to be heated), or conversely decreasing the heating effect or agitation in areas which are determined to have a temperature closer to the target temperature to which the sample is to be heated, i.e. at those areas which have thawed quickest.

In further embodiments the method may comprise using one or more sensors to monitor structural characteristics of the sample. For example, in some embodiments the method may comprise using one or more structural sensors to determine the ice fraction of the sample. In embodiments wherein the method comprises heating/thawing a sample, the one or more structural sensors may be used to monitor the changes in the ice fraction of the sample as it thaws/heats. The method may further comprise varying the heating profile and/or agitation provided by, for example, increasing the heating effect or agitation at areas which have a high ice fraction, or conversely decreasing the heating effect or agitation at areas which have a low ice fraction, i.e. at those areas which have thawed quickest. For example, the agitation may be changed when a particular ice fraction is determined to be present in the sample, e.g. when the sample is less than 99, 95, 90, 85, 80, 75, 70, 65, 60, 55, 50, 45, 40, 35, 30, 25, 20, 15, 10 or 5% ice in volume, or particularly, wherein less than 99, 95, 90, 85, 80, 75, 70, 65, 60, 55, 50, 45, 40, 35, 30, 25, 20, 15, 10 or 5% of the water in the sample is ice.

In some embodiments the method may comprise using two or more different types of sensor to monitor two or more different characteristics of the sample, sample container or the members.

Each of the plurality of members may be independently moveable with respect to one another against said bias under the application of a force on at least a portion of the member. As indicated above, the container is contacted with one or more of a plurality of members in the method of the invention. In this respect, the container may only contact a portion of the plurality of members which are present. In such embodiments only those members which are brought into contact with the container may move with respect to the remaining members against the bias, with the remaining members being retained in the resting position. For example, in some embodiments the method may comprise contacting the container (comprising the sample) with at least 10%, 15%, 20%, 25%, 30%, 35%, 40%, 45%, 50%, 55%, 60%, 65%, 70%, or 75% of the members present e.g. in a device of the invention. The number of members brought into contact with the container will be dependent on the size of the container itself and the number of members. Where a sample container is of equal size to the members present (e.g. in a device of the invention), the method may comprise contacting the container with each of the plurality of members.

In some embodiments the method may comprise contacting the container with one or more of the plurality of members by placing the container on top of one or more of the members. The plurality of members may be provided in a single horizontal plane. In such embodiments, those members in contact with the container are moved against their bias under the weight of the container and/or the sample contained therein.

In further embodiments the method may comprise contacting the container with one or more of the plurality of members by placing the container in an abutting relationship against one or more of the members. The plurality of members may be provided in a plane which in some embodiments may comprise a substantially vertical plane. In such embodiments, those members in contact with the container are moved against their bias by means of the abutment of the container with the one or more members.

In some embodiments the method may comprise placing the container between two or more planes of members. For example, in some embodiments the method may comprise placing the container between two substantially horizontal planes of members. In such embodiments the method may comprise placing the container on top of a first horizontal plane of members, and subsequently placing a second horizontal plane of members onto an opposing surface of the container to the first horizontal plane of members. In this way, the method of the invention provides a means to heat or cool two opposing surfaces of the sample.

In further embodiments the method may comprise placing the container between two substantially vertical planes of members. In such embodiments the method may comprise placing the container in an abutting relationship with both a first vertical plane of members and a second vertical plane of members. Again, by placing the container between the two planes of members in this manner, the method provides a means to heat or cool two opposing surfaces of the sample but in a different orientation to the horizontal configuration as set out above.

In some embodiments the method may comprise placing the container into a substantially tubular recess formed by two or more of the plurality of members, with the members surrounding the container and the sample contact surfaces of the two or more members defining the walls/surfaces of the recess. For example, in some embodiments the method may comprise placing the container into a recess which is substantially cylindrical, triangular, square, rectangular or other polygonal-shaped cross-section, which may or may not be complimentary to the shape and configuration of a sample or sample container.

In some embodiments the method may comprise applying an additional force onto a surface of the sample. The force may be applied to increase the extent to which one or more of the members are moved against their bias. This may be done to ensure a uniform heating/cooling profile across the sample and/or to shape the sample during heating or cooling. For example, in such embodiments, a force may be applied to the sample such that those members already in contact with the sample are pushed further against their bias, thereby enabling members which would not otherwise be in contact with a surface of the sample to come into contact with the sample. This may be particularly useful in embodiments wherein the method comprises heating or cooling a sample on a horizontal or substantially horizontal plane of members, wherein the weight of the sample is not sufficient to move one or more of the members against their bias. The force may be applied to at least a portion of a surface of the sample. In preferred embodiments the force is applied to an opposing surface of the sample in contact with one or more of the members. The method may comprise using a further component, such as a plate, which may be a flat plate, and placing the further component onto a surface of the sample in order to apply the additional force. In some embodiments, such as those wherein the method comprises heating or cooling a sample on a horizontal or substantially horizontal plane of members, the weight of the further component may provide the additional force. Alternatively, the further component may additionally be held in position against a surface of the sample. The further component may comprise a lid or cover which is moveable to a position wherein it overlies one or more of the members, which when in this position may provide the additional force onto a surface of the sample. The further component may itself comprise, or be connected to, one or more heating and/or cooling members, in embodiments which the further component is in substantially flat plate it may be connected to, or comprise, a plane or members.

In some embodiments the method may comprise controlling the operation of at least one of the plurality of members, or at least one group of members independently from each of the other members or groups of members. For example, in embodiments wherein the method comprises using members to heat or thaw a sample, the method may comprise independently controlling the heat energy transferred to each member, or group of members, via the one or more heat sources/heating elements.

In embodiments wherein the method comprises cooling a sample, the method may comprise controlling the temperature of one or more of the members, or groups of members, independently to control the extent to which the heat energy within a section or sections of the sample or samples is transferred to the members. For example, where a section or sections of the sample or samples is to be cooled more quickly than another section/s, the temperature of the corresponding member or members in contact with the first section or sections may be reduced with respect to each of the remaining members or groups of members.

In this way, the method allows the sample or samples to be spatially differentially heated or cooled by choosing the section or sections of the sample or samples which are heated/cooled, wherein the section or sections may be separated from one another. This is particularly advantageous in embodiments wherein the sample or samples are dimensioned such that only a portion of the members are in contact with the sample/s during the heating or cooling process. In such embodiments, the method comprises choosing to heat/cool only those members or groups of members which are in contact with the sample/s or sample container.

In some embodiments the method comprises heating or cooling various regions of a single sample differentially, or indeed each of a plurality of different samples differentially. This is particularly advantageous, for example, in embodiments wherein it may only be necessary to heat/cool the portion of the container within which the sample/samples are contained.

In further embodiments the method may comprise temporally differentially heating or cooling a sample or samples. For example, in embodiments wherein the method comprises heating the sample, the method may comprise independently controlling when and to what extent heat energy is transferred to each member, or group of members, via the one or more heat sources/heating elements. In this way, the method provides a way to heat different sections of the sample or samples at different times. In embodiments wherein the method comprises cooling a sample or samples using cooling members, the method may further comprise controlling the temperature of one or more of the members, or groups of members, independently to control when and to what extent heat energy within a section or sections of the sample or samples is transferred to the members. For example, the method may comprise varying the temperature of one or more of the members or groups of members over time to temporally vary the extent to which heat energy within a section or sections of the sample or samples is transferred to said members.

In some embodiments, the method may comprise controlling the extent to which at least 1, or at least 2, or at least 3, or at least 4, or at least 5, or at least 6, or at least 7, or at least 8, or at least 9 or at least 10 discrete regions of a sample may be heated or cooled independently. In some embodiments the method may comprise temporally varying the extent to which the at least 1, 2, 3, 4, 5, 6, 7, 8, 9 or 10 discrete regions of a sample may be heated or cooled, the temporal variation of the heating or cooling of each discrete region being independent of the remaining regions.

In some embodiments the method may additionally comprise agitating the sample. The agitation of the sample may involve vibrating, shaking, stirring, rotating, rolling, squeezing, displacing, prodding, or flexing the sample, for example. The agitation may be temporally varied. For example, the agitation may be performed at a particular frequency and/or amplitude and/or for a particular time period e.g. from at least 10, 20, 30, 40, or 50 seconds to at least 1, 2, 3, 4, 5, 6, 7, 8, 9 or 10 minutes. The particular agitation selected for a given sample will depend on the sample which is initially provided, i.e. on physical characteristics of the sample and on the container type/volume and/or the volume of sample material and optionally on the thermal conductivity of the container itself. Alternatively or additionally, the container, e.g. its volume and geometry will dictate the required agitation. In some embodiments, wherein the container is a vial or tube, orbital agitation may be adopted and in other embodiments, where the container is a bag, squeezing, displacing, prodding and/or flexing may be adopted.

In some embodiments the agitation may be spatially varied. For example, different sections or regions on the sample may be agitated to a greater or lesser extent to other sections or regions of the sample.

In some embodiments the method may comprise heating or cooling a sample comprised within a bag or other flexible container. In such embodiments, the method may comprise heating or cooling the sample by placing the bag or other flexible container on top of a single plane of members or between two planes of members. In presently preferred embodiments the method comprises heating or cooling a sample contained within a bag or other flexible container by placing the container between two horizontal planes of members.

The method may comprise heating or cooling a sample comprised within a vial. In such embodiments, the method may comprise heating or cooling the sample by placing the vial between two planes of members. In presently preferred embodiments the method comprises heating or cooling a sample comprised within a vial by placing the container between two vertical planes of members.

According to a third aspect of the present invention there is provided the use of a device in accordance with the first aspect of the invention to heat or thaw a sample.

According to a fourth aspect of the present invention there is provided the use of a device in accordance with the first aspect of the present invention to cool or freeze a sample.

DETAILED DESCRIPTION OF THE INVENTION

In order that the invention may be more clearly understood embodiments thereof will now be described, by way of example only, with reference to the accompanying drawings, of which:

Figure 11:
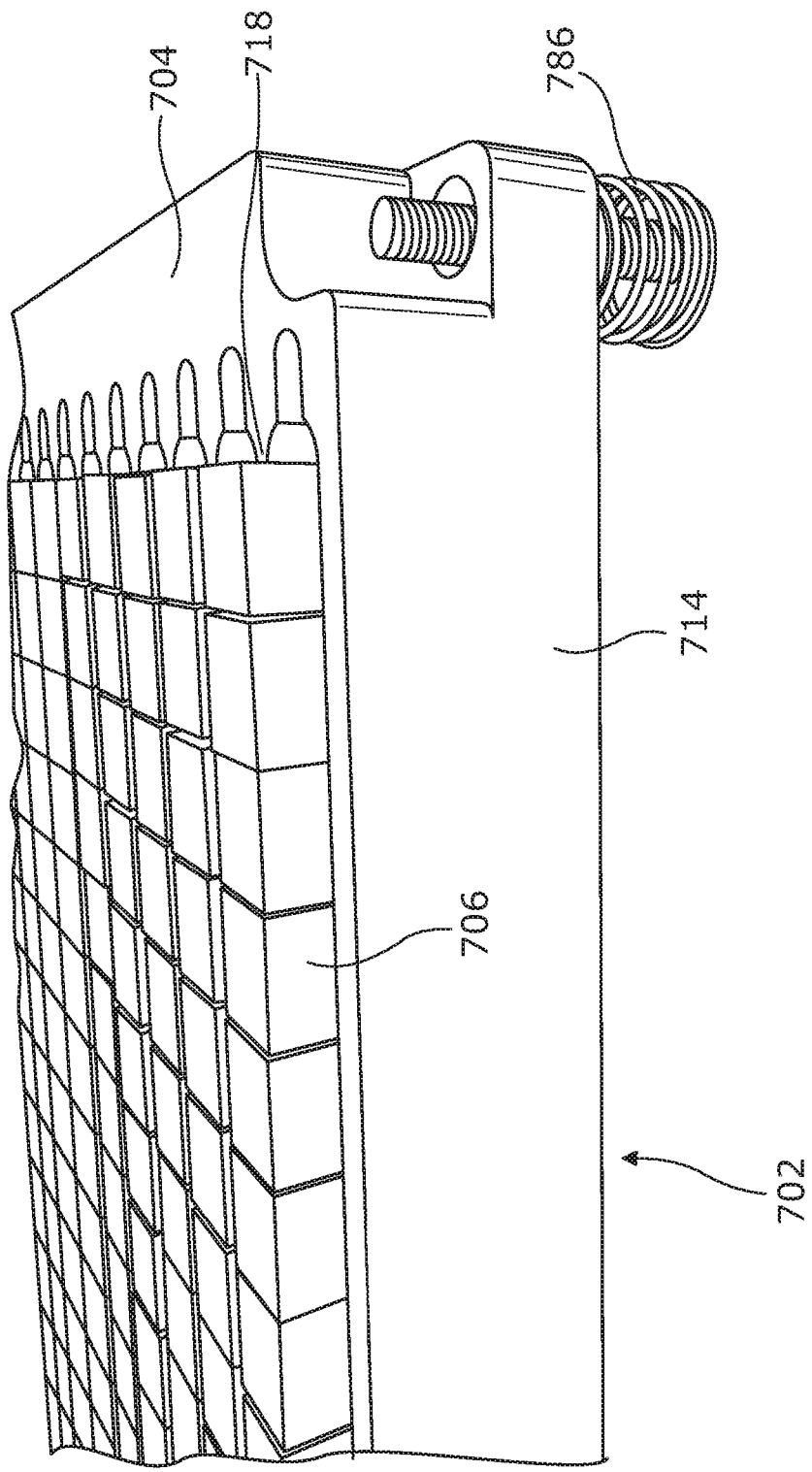
Figure 12:
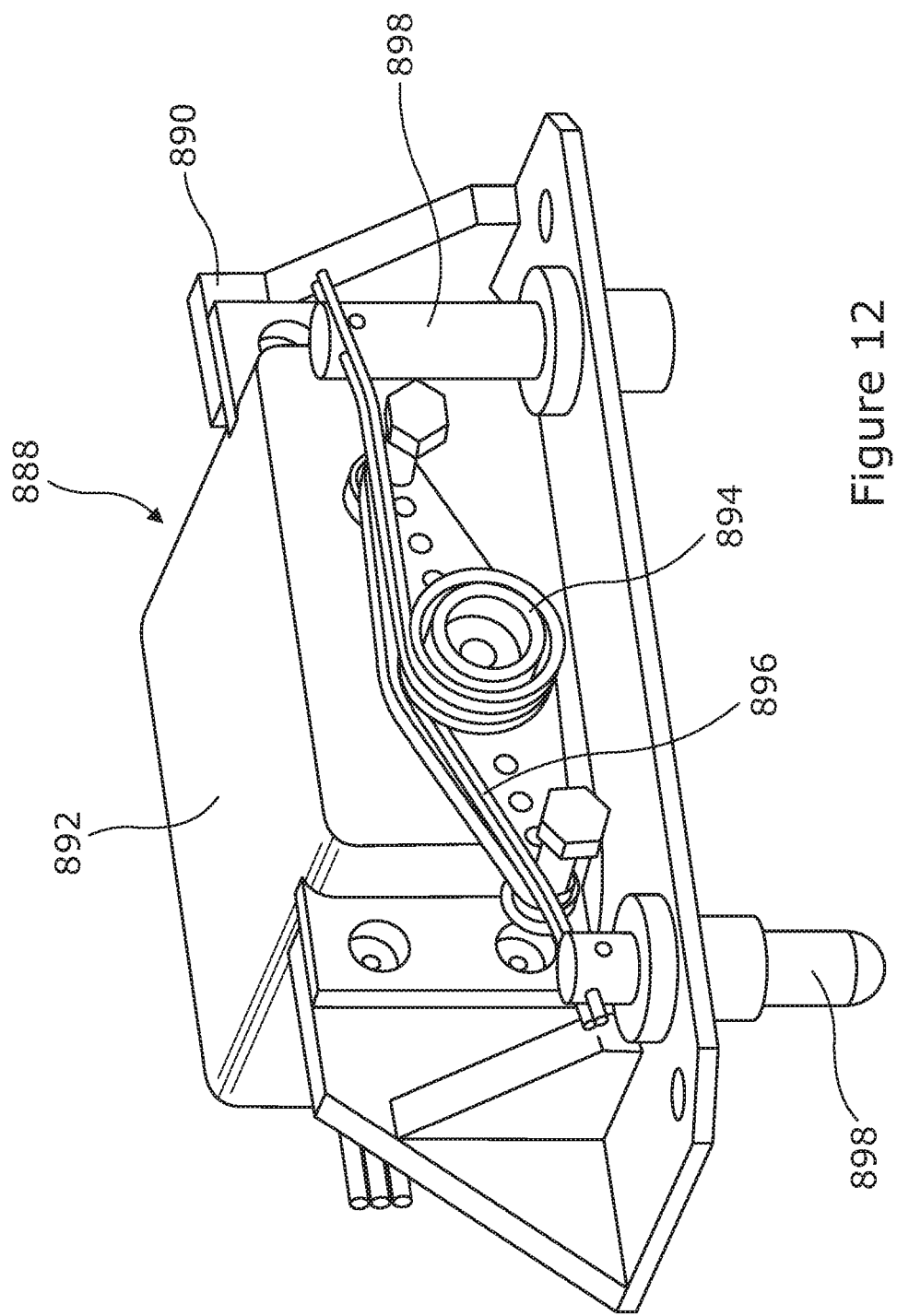
Figure 13:
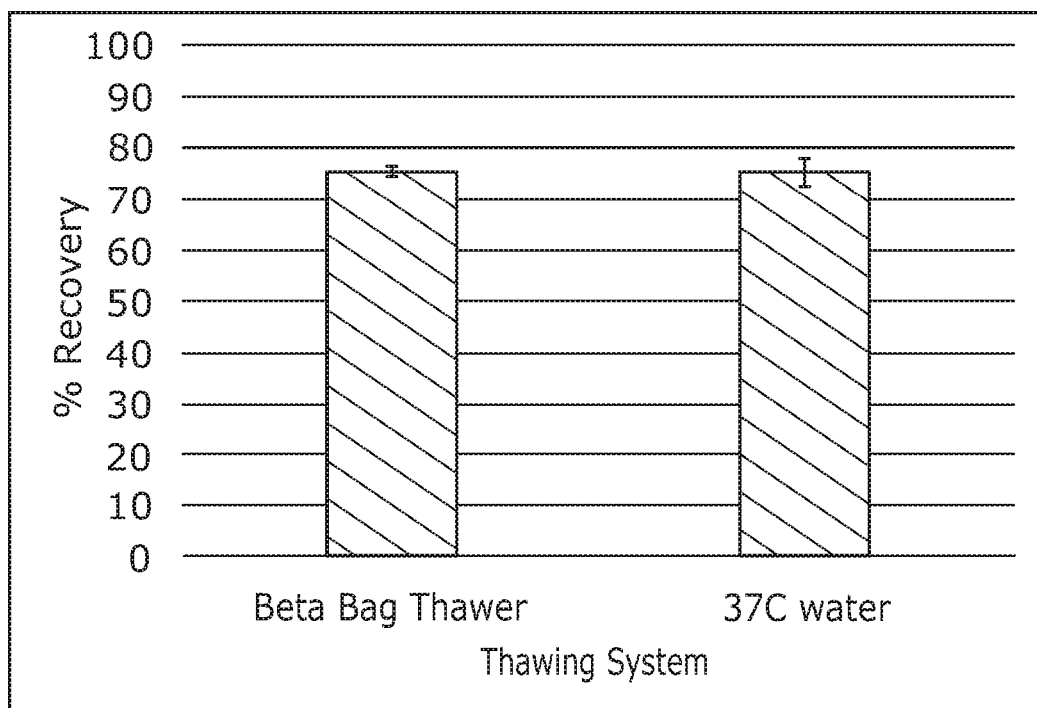
Figure 14:
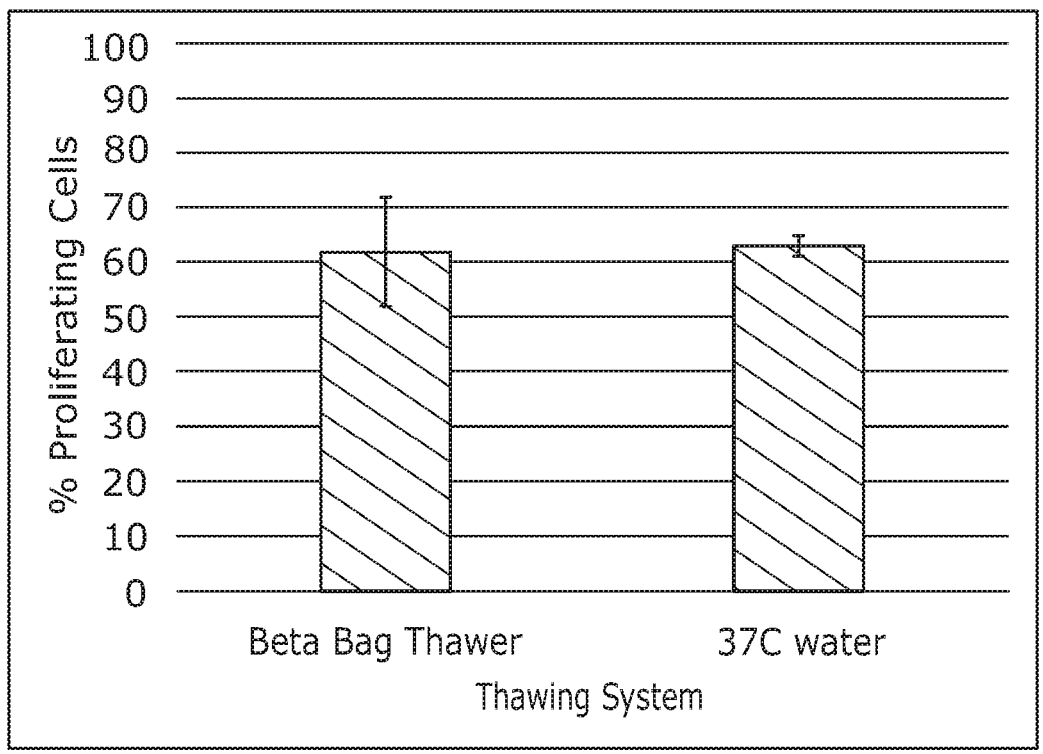
Figure 15:
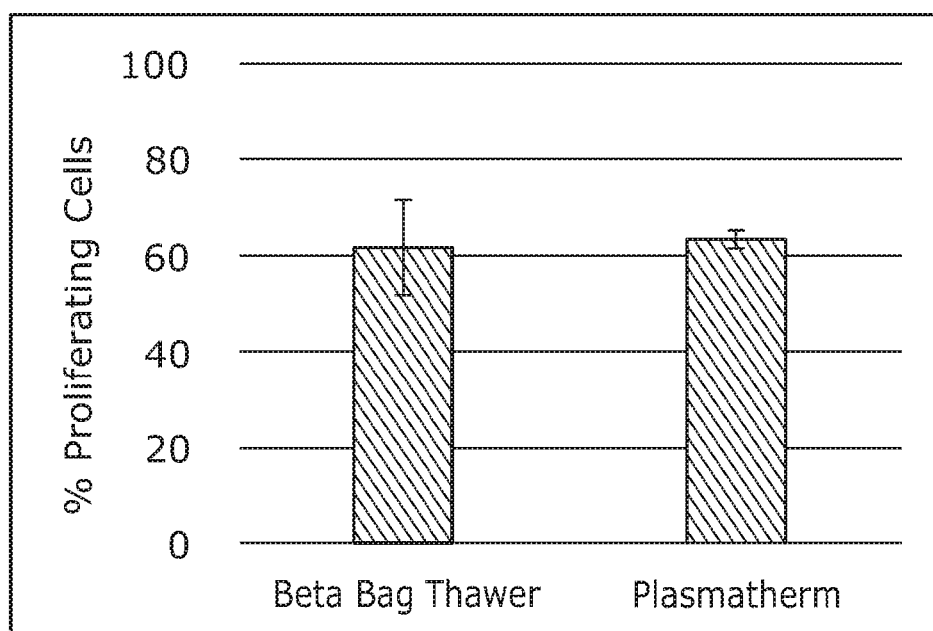
Figure 16:
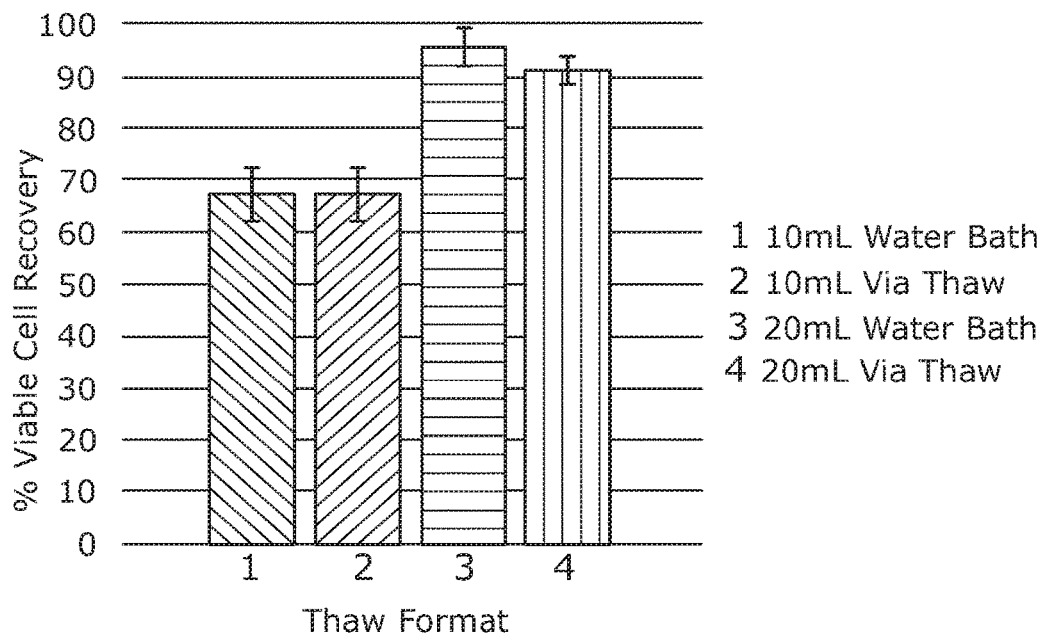
Figure 17:
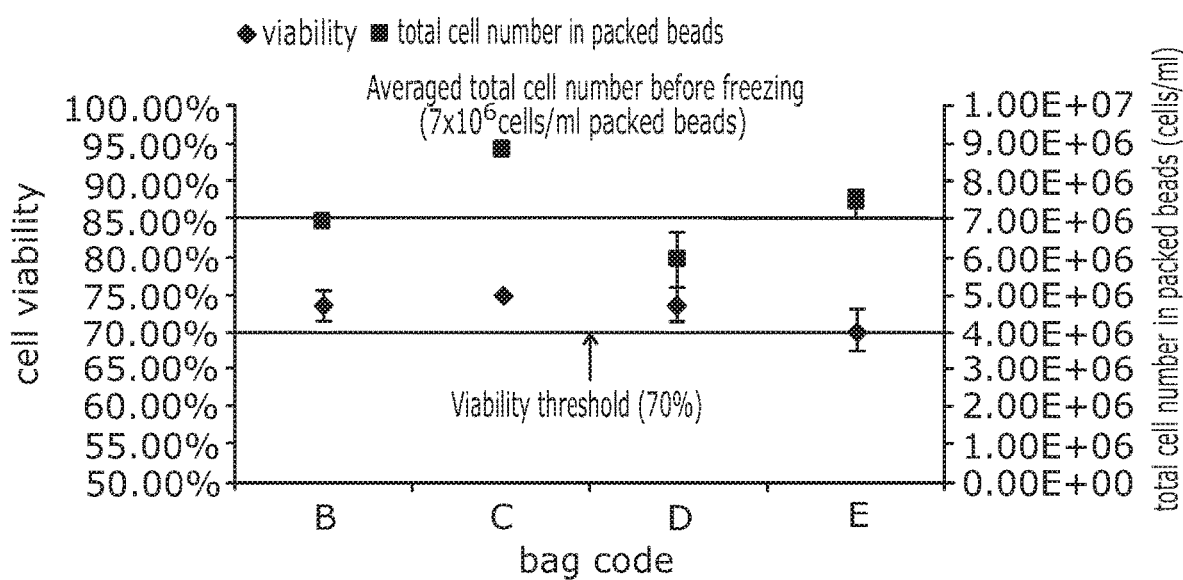

FIGS. 10A-D are a series of perspective views of a device in accordance with a yet further embodiment of the invention in different stages of assembly and from different angles;

FIG. 11 is a perspective view of part of a further embodiment of a device in accordance an aspect of the invention;

FIG. 12 shows a force-limited oscillating agitator which can be incorporated into a device in accordance with the invention;

FIG. 13 is a graph showing a comparison of the effectiveness of methods of the invention compared with prior art techniques;

FIG. 14 is a further graph showing a comparison of the effectiveness of methods of the invention compared with prior art techniques;

FIG. 15 shows a comparison between using the prototype device of the invention (named the beta bag thawer) to thaw a frozen cell sample, as compared to a Plasmatherm system (Barkley), which uses bladders that are fluid filled from a reservoir below that pumps water around to thaw bag samples;

FIG. 16 shows the results from thawing 10 ml and 20 ml volumes of T-cells using both a water bath and the prototype device of the invention (referred to as "Via Thaw". There was no significant difference in the % of viable cell recovery seen between the two volumes and the two devices; and FIG. 17 shows the cell viability of thawed hepatocytes using a prototype device of the invention.

Figure 1:
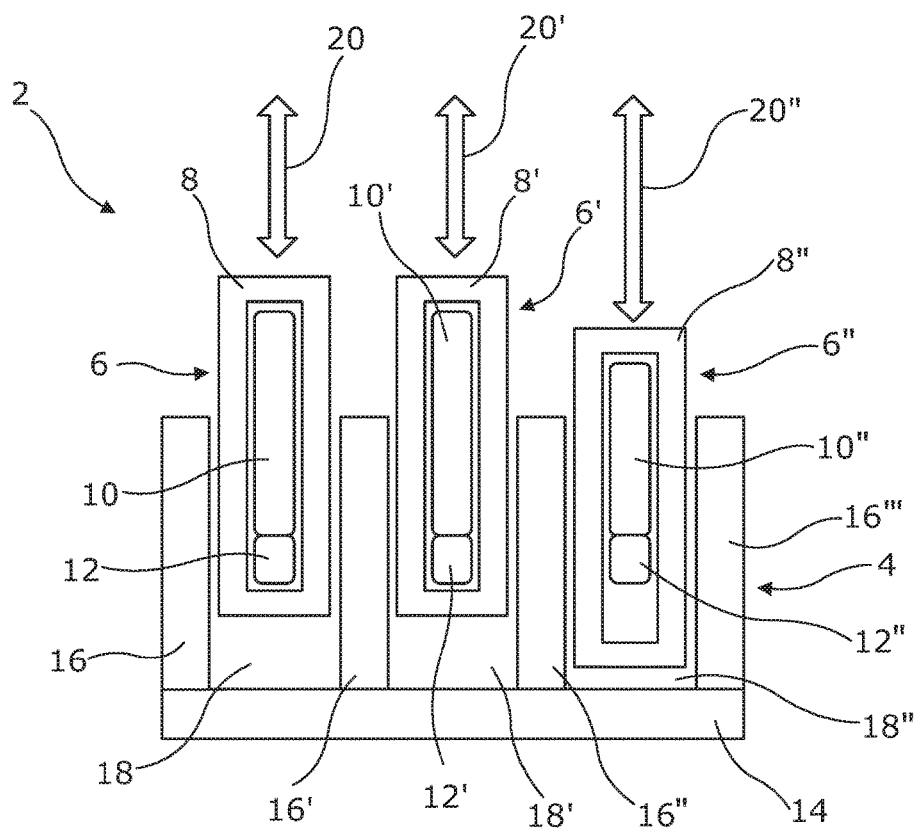
FIG. 1 is a side cross sectional view of a portion of a first embodiment of a device in accordance with the invention.

FIG. 1 illustrates a portion of a first embodiment of a device 2 of the invention. The device comprises a heating device 2 which comprises an integral heating plate 4, and a series of members in the form of heating members 6, 6', 6" which are independently moveable with respect to the heating plate 4 in the direction of arrows 20, 20', 20", respectively. It should be understood that FIG. 1 illustrates a portion of the heating device 2 only. Heating device 2 may comprise any number of additional heating members (see FIG. 2).

Each of the heating members 6, 6', 6" comprises a sample contact surface 8, 8', 8" which surrounds a biasing means in the form of respective resilient members 10, 10', 10" which bias their respective members 6, 6', 6" to the position illustrated by heating members 6 and 6'. Each of the members 6, 6', 6" is moveable against this bias under the application of a force onto the contact surface 8, 8', 8" which, for example, may be provided by laying an object on top of the members 6, 6', 6". This is illustrated by the position of heating member 6". In addition, each heating member 6, 6', 6" is provided with a support member 12, 12', 12" which controls the extent to which the respective heating member 6, 6', 6" may be moved against the bias provided by resilient members 10, 10', 10". This is to ensure that heating members 6, 6', 6" remain physically separated from the heating plate 4.

Heating plate 4 comprises a base plate 14 and a series of upwardly extending walls 16, 16', 16", 16''' which form a series of wells 18, 18', 18" in the heating plate 4 within which heating members 6, 6', 6" are located, in use. As illustrated, the heating members 6, 6', 6" may move in a vertical direction along the wells 18, 18', 18" against the bias provided by resilient members 10, 10', 10". By providing wells 18, 18', 18" in the heating plate 4, this ensures that each heating member 6, 6', 6" is substantially surrounded by the heating plate 4 increasing the rate of heat transfer from the plate 4 to the members 6, 6', 6", in use.

Figure 2:
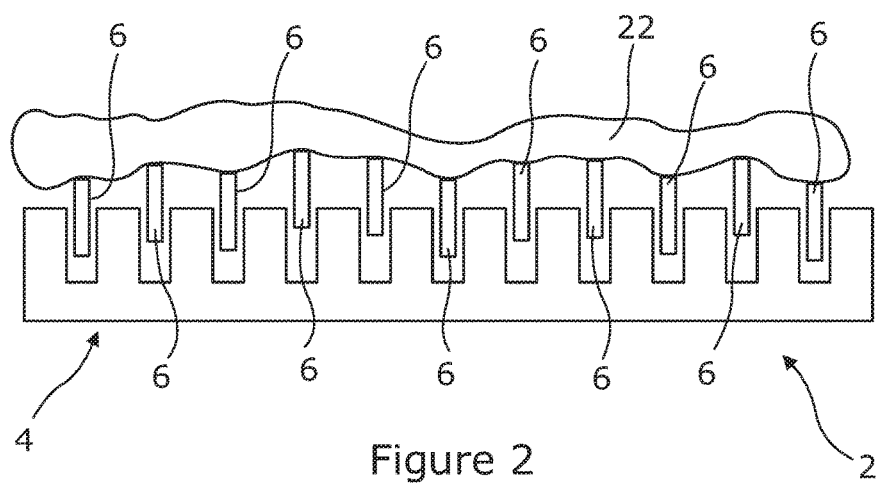
FIG. 2 is a further side cross sectional view of the device of FIG. 1.

FIGS. 1 and 2 illustrate a heating plate 4 which comprises a base plate 14 and a series of upwardly extending walls 16, 16', 16", 16'''. In some embodiments the base plate 14 and upwardly extending walls 16, 16', 16", 16''' may be separate components, but are preferably integrally formed to form heating plate 4. In embodiments wherein the components of heating plate 4 are integrally formed, the plate 4 may be formed through extrusion or through deposition of a given material into a mold for forming a singular heating plate 4.

Although not shown in FIGS. 1 and 2, heating plate 4 may be connected to a power supply. In use, the power supply may supply an electric current to or through the heating plate 4 which may subsequently increase in temperature via resistive heating or other equivalent means. Alternatively, the heating plate 4 may be heated via an external heat source, such as an open flame or the like.

The operational use of a series of embodiments of the invention is illustrated in FIGS. 2 to 5. Where components of different embodiments are substantially identical, like reference numerals have been used.

FIG. 2 is a cross sectional view of the embodiment of the heating device 2 shown in FIG. 1 illustrating how the device 2 may be used to heat/thaw a sample located within a flexible container in the form of bag 22.

In order to transfer heat energy ultimately to the sample within bag 22, first the temperature of the heating plate 4 itself is increased. This may be achieved, as described above through resistive heating by passing an electrical current through the heating plate 4, or by subjecting the plate 4 to an external heat source, such as an open flame, for example. Once the heating plate 4 is at an increased temperature with respect to the ambient temperature of its surroundings, heat energy is transferred to each of the heating members 6 across the gap between the plate 4 and the members 6. This may occur via conduction through or convection of air molecules within the gap itself, or through the heating plate 4 radiating heat which is subsequently absorbed by the heating members 6. The temperature of the heating members 6 thereby increases and through contact with the bag 22, heat energy is subsequently transferred to the sample in order to heat or thaw the sample.

As shown, bag 22 comprises an undulating outer surface which may have been formed due to flexing of the bag during freezing of the sample. In use, the bag 22 is laid across the heating members 6 and the weight of the bag 22 and the sample contained therein is sufficient to move the members 6 against the bias provided by their respective biasing means (which in this embodiment comprise resilient members as shown in FIG. 1). By making each of the heating members 6 independently moveable with respect to the heating plate 4, the members 6 can conform to the undulating surface of the bag 22 ensuring contact between the heating members 6 and the bag 22 along the entire length of the bag 22. In this way, the heat transfer from the heating device 2 to the sample within the bag 22 can be made substantially uniform across the entire bag 22.

Figure 3:
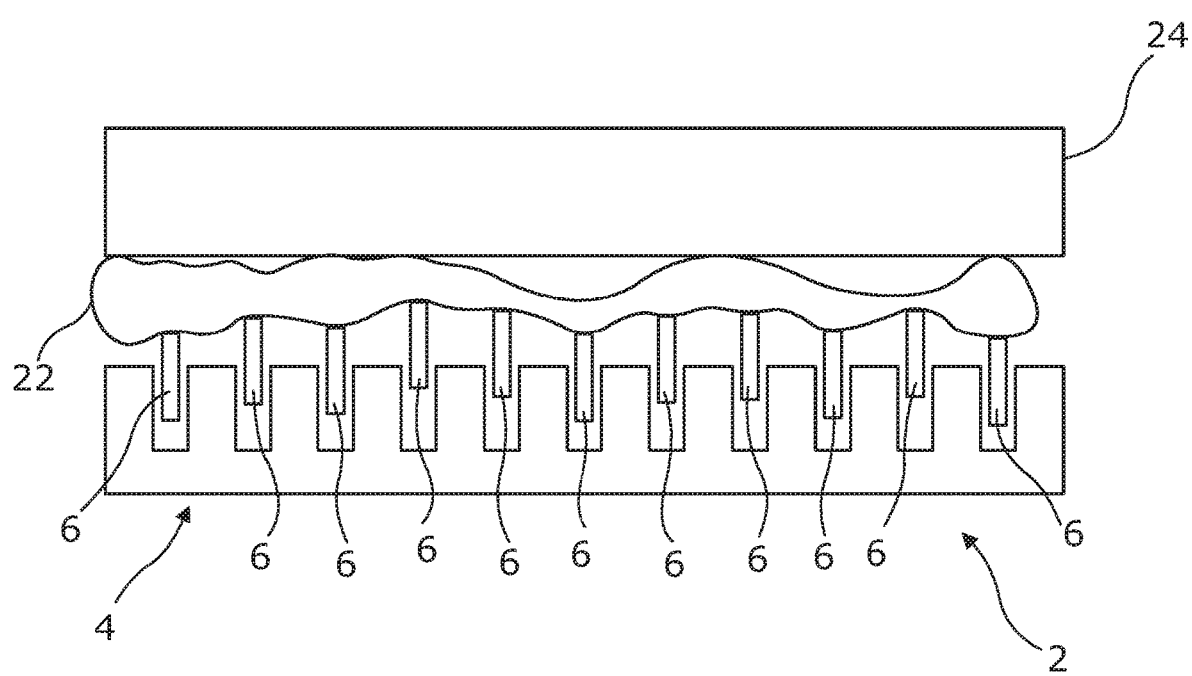
FIG. 3 is a side cross sectional view of a variant of the device shown in FIGS. 1 and 2.

FIG. 3 illustrates the operational use of a variant of a heating device 2 of the invention showing how the device 2 may be used to heat/thaw a sample located within a flexible container in the form of bag 22.

FIG. 3 illustrates embodiments wherein the device 2 additionally comprises a means to apply an additional force to the members 6 in the form of a lid or cover 24 which covers one or more of the heating members 6. As shown, in use, the lid 24 may contact an opposing surface of the sample 22 in order to increase the force acting downwards onto the heating members 6. Embodiments of this type may be particularly useful in instances where the weight of sample 22 is not great enough to sufficiently compress the resilient members 10 within the heating members 6 and as a result many of the heating members may not contact a portion of the surface of the sample 22. Lid 24 is therefore employed to provide a great enough force such that a significant proportion of the heating members 6 are in contact with the sample 22 in use.

Figure 4:
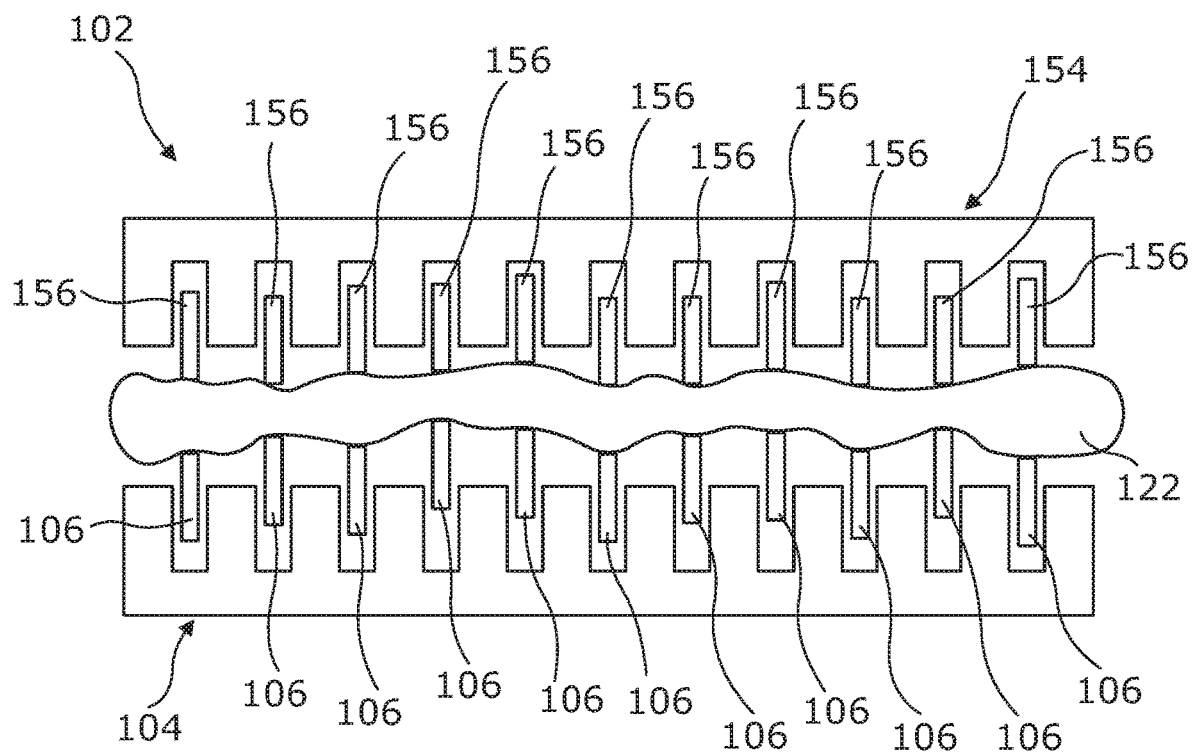
FIG. 4 is a side cross sectional view of a second embodiment of a device in accordance with the invention.

FIG. 4 illustrates the operational use of a second embodiment of a heating device 102 of the invention showing how the device 102 may be used to heat/thaw a sample located within a flexible container in the form of bag 122.

Heating device 102 is similar to device 2 shown in FIGS. 1 to 3 in that it also comprises a heating plate 104 having a series of wells each containing a heating member 106. Furthermore, as with heating device 2, heating members 106 are each independently moveable with respect to the heating plate 104 in the same way that heating members 6 are moveable with respect to heating plate 4 and therefore conform to the shape of bag 122 when the bag 122 is placed on top of heating members 106.

Heating device 102 differs from device 2 in that it also comprises a secondary heating plate 154. Secondary heating plate 154 is substantially identical to heating plate 104 in that it too comprises a series of wells which each contain a heating member 156. Again, heating members 156 are moveable within said wells and are biased to a first position and moveable from the first position under the application of a force to the member 156 itself. In use, heating plate 154 is laid on top of the bag 122 such that the heating members 156 are brought into an abutting relationship with an opposing surface of bag 122 to heating members 106. In this case, the abutment between the heating members 156 and the surface of the bag 122 acts to move the members 156 against their respective bias such that the heating members 156 conform to the shape of the opposing surface of the bag 122. In this way, the device 102 provides a means to heat two opposing sides of a sample in a uniform manner. In a variant of the embodiment of FIG. 4, the secondary heating plate 154 may also act as a means to apply an additional force to the bag 122 (or any other sample).

Figure 5:
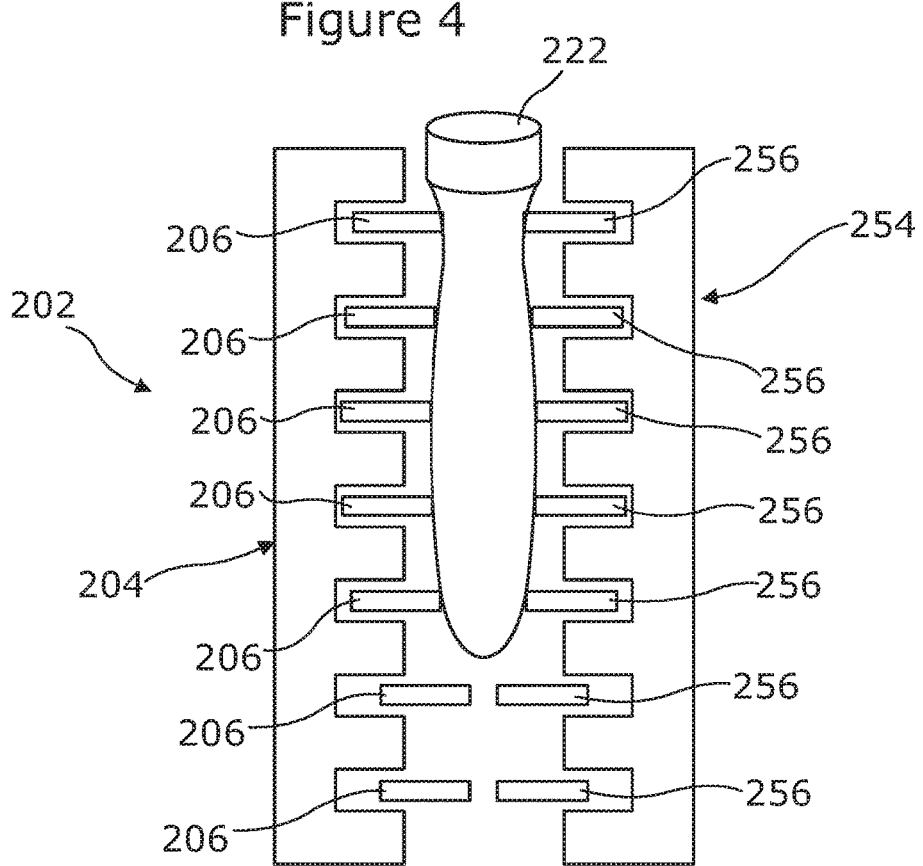
FIG. 5 is a side cross sectional view of a third embodiment of a device in accordance with the invention.

FIG. 5 illustrates the operational use of a third embodiment of a heating device 202 of the invention showing how the device 202 may be used to heat/thaw a sample located within a container in the form of a vial 222.

As with heating device 102 shown in FIG. 4, device 202 comprises a pair of heating plates 204, 254 each comprising a plurality of heating members 206, 256 independently moveable along individual wells within the heating plate 204, 254 itself. Heating device 202 differs from device 102 in that it may be used in a vertical orientation, as shown. This is particularly beneficial in cases whereby the sample may be within a container, such as the vial 222, which needs to remain upright at all times or indeed where the sample itself needs to remain in a certain orientation.

Heating plates 204, 254 are substantially identical to heating plate 154 of heating device 102 in that the respective heating members 206, 256 are brought into an abutting relationship with a surface of vial 222, rather than placing the vial 222 on top of the members 206, 256. The abutment between the heating members 206, 256 and the respective surfaces of the vial 222 acts to move the members 206, 256 against their bias such that the heating members 206, 256 conform to the shape of the respective surfaces of the vial 222. In this way, the device 202 provides a means to heat two opposing sides of a sample in a uniform manner which is provided in a vertical orientation.

In alternative arrangements, the heating plates 204, 254 may be replaced with two or more members which are arranged to form a substantially cylindrical recess into which a container, which may be a vial 222 or other cylindrical container, may be placed, rather than between the two plates 204, 254 as shown. In some embodiments the formed recess may not be cylindrical, but may comprise a substantially triangular, square, rectangular or other polygonal-shaped cross-section, which may or may not be complementary to the shape and configuration of a sample or sample container placed in the recess.

Furthermore, although FIGS. 2 to 4, and FIG. 5 have been discussed as being directed at heating or cooling samples contained within a bag 22, 122 or a vial 222, respectively, it should be understood that either of the embodiments shown in these Figures may be used to heat or cool samples within a bag 22, 122 or within a vial 222. For example, when the device comprises that shown in FIGS. 2 and 3, the sample/s may be contained within a vial 222 which comprises a lid or cover on an open end thereof to prevent leakage of the sample from vial 222. In embodiments such as that shown in FIG. 4, it should be understood that the device may be used to heat or cool samples contained within a bag 22, 122 by placing the bag between the opposing heating plates 204, 254. A device in accordance with the invention may be used to heat or thaw any type of sample. However, the invention is particularly suited to cases wherein there is a requirement for the sample to remain uncontaminated. For example, the sample may be biological material or even food products.

FIGS. 1 to 5 are cross sectional views of embodiments of devices 2, 102, 202 in accordance with the invention. As such, the Figures illustrate a single row of heating members only. However, it is to be understood that the samples would be contained within a three-dimensional container. Therefore, in order to provide a uniform heat transfer across the whole of the container, the heating members may be provided in a series of rows forming a plane or matrix of heating members.

Figure 6:
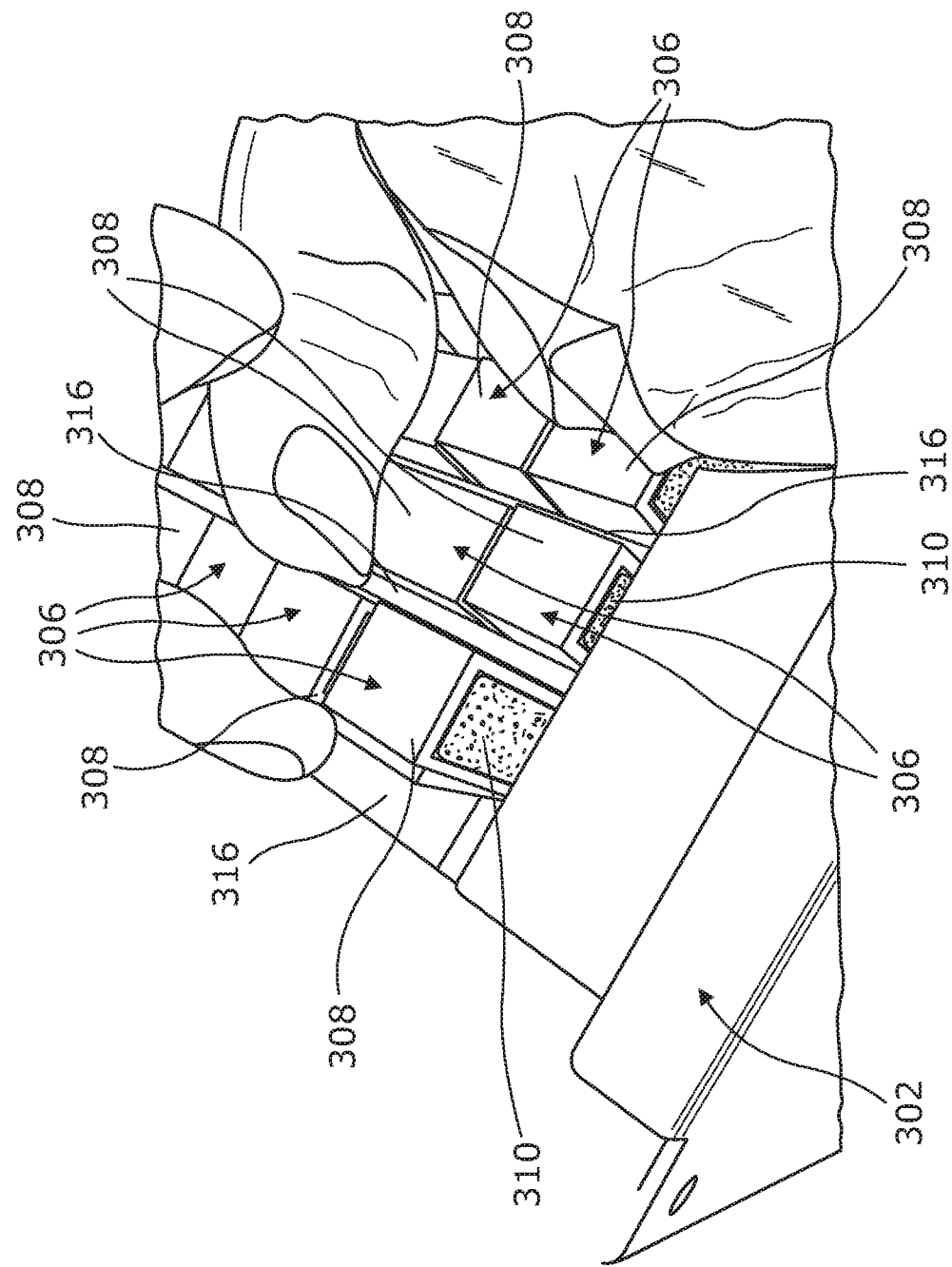
FIG. 6 is a perspective view of a further embodiment of a device of the present invention.

FIG. 6 is a perspective view of a device of the invention. The device comprises a heating device 302 which comprises an integral heating plate (not visible), and a series of rows of heating members 306. Each of the heating members 306 within the rows are independently moveable with respect to the heating plate and comprise a sample contact surface 308 which surrounds a biasing means in the form of respective resilient members 310, the operation of which has been discussed above with reference to FIG. 1. In FIG. 6, a number of the heating members have been manually raised for illustrative purposes only.

The heating plate comprises a base plate (not visible) and a series of upwardly extending walls 316 which form a series of wells in the heating plate within which heating members 306 are located. As discussed above, the heating members 306 may move in a vertical direction along the wells against the bias provided by resilient members 310. By providing wells in the heating plate, this ensures that each heating member 306 is substantially surrounded by the heating plate increasing the rate of heat transfer from the plate to the members 306, in use.

In some embodiments of the devices of FIGS. 1-6, heating members 6, 6', 6", 106, 206, 306 may be provided with a flexible membrane which may cover the sample contact surface 8, 8', 8" and be positioned, in use, between the members 6, 6', 6", 106, 206, 306 and the sample 2, 122, 222 to prevent contaminants and/or portions of the sample 2, 122, 222 from falling or moving between spaces between adjacent heating members 6, 6', 6", 106, 206. An embodiment of this flexible membrane is shown in FIGS. 7 and 8 as is discussed below.

Figure 7:
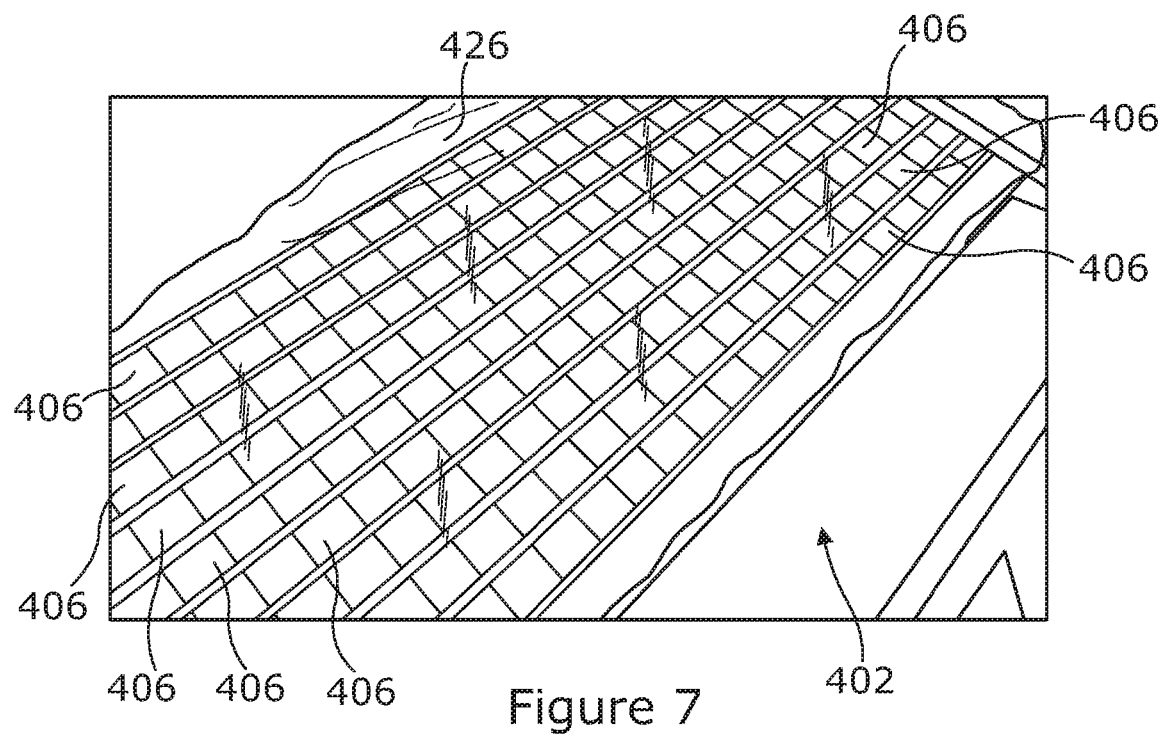
FIG. 7 is a further perspective view of a still further embodiment of a device in accordance with of the present invention.
Figure 8:
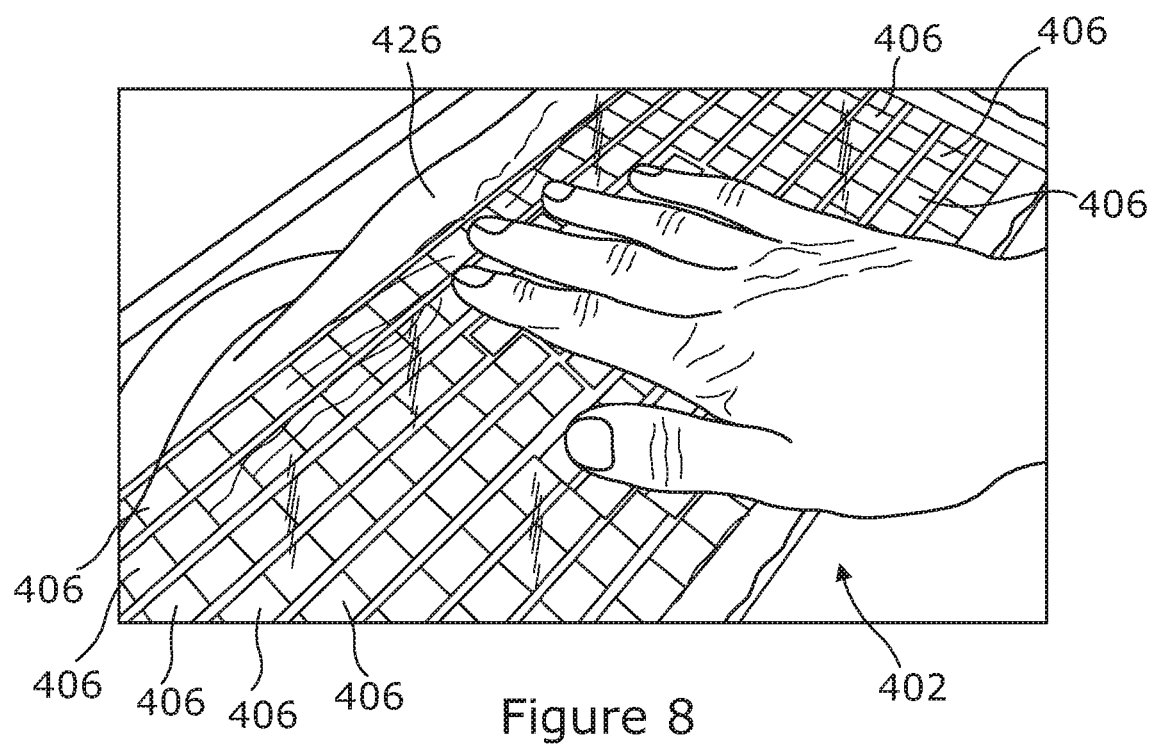
FIG. 8 is a further perspective view of the device of FIG. 7.

FIGS. 7 and 8 are further perspective views of a device of the invention. The device shown is a heating device 402 including a plurality of rows of heating members 406. As discussed above, FIGS. 7 and 8 additionally illustrate the use of a flexible membrane 426 placed over the top of the plurality of rows of heating members 406. The flexible membrane 426 is preferably formed from a thermally conductive material, which may be silicone, latex rubber, polyurethane, polyethylene, methacrylate-based resins, EVA for example, and is operable in use to prevent any contaminants or portions of one or more samples or sample container from falling or moving between any spaces between adjacent members 406. The flexible membrane is typically attached to a frame or supporting structure surrounding the heating members 406. The flexible membrane 426 is not taut so that the sample is able to make contact with the heating members 406 indirectly through the sheet and to maintain contact as the heating members deflect under the weight of the sample and/or other applied force. The flexible membrane 426 will therefore create a depression or bowl type effect beneath the sample in which any liquid which spills or is given off as the sample thaws is collected. After thawing, the whole membrane 426 can be lifted off the device with the liquid contained in the middle.

FIGS. 7 and 8 also illustrate an operational use of the heating members 406. In particular, FIG. 7 shows the heating members 406 in a rest position with no additional forces applied thereto in order to move the members 406 against their bias (as described above). FIG. 8, on the other hand, illustrates how those heating members 406 in contact with a sample, in this Figure illustrated by a person's hand pressing down on the members 406, move against the bias. Those heating members 406 not in contact with the sample are not moved against their bias. In this way, the heating members are shown to be independently moveable in order to conform to the shape of a sample placed thereon or against, depending on the orientation of the device 402 as a whole, to provide a uniform heating profile across the sample, in use.

The embodiments shown in the drawings each illustrate a device and method of using said device to heat or thaw samples. However, it should be understood that the device of the invention is not limited to heating and thawing. Rather, the device may be used to cool or freeze samples also by configuring the members to remove heat energy from a sample in order to reduce the temperature of the sample. Where the device is used to cool a sample, it will be appreciated that the heating plates could be modified to provide a cold source and in such embodiments these may be referred to as cooling plates. Such features may be referred to more generally as thermal plates or thermal elements, especially in devices which can be used alternatively to heat or cool samples.

The devices 2, 102, 202, 302, 402 may additionally comprise a means to differentially heat (or cool) the sample, rather than providing a uniform heating profile as shown in these Figures. For example, each of the heating members 6, 6' etc. or indeed groups/planes of heating members may be independently controllable in order to vary the temperature profile across the members. In this way, specific regions on the sample may be heated/cooled to different temperatures as is required.

The differential heating/cooling of the sample may additionally or alternatively comprise varying the temperature profile across the members temporally. In this way, the sample, or regions of the sample may be heated/cooled at different times.

Furthermore, the devices 2, 102, 202, 302, 402 may additionally comprise a means to agitate the sample. For example, each of the heating members 6, 6' etc. or indeed groups/planes of heating members may be operable to vibrate or oscillate in order to agitate the sample. Such embodiments are particularly useful where the device 2, 102, 202, 302, 402 is being used to heat/thaw a sample. In some embodiments the movement of the members 6, 6' etc. may be independently controllable in order to vary the agitation profile across the members. In this way, specific regions on the sample may be agitated to different extents as is required. The agitation of the sample may additionally be varied temporally. In this way, the sample, or regions of the sample may be agitated at different times.

Referring back to FIGS. 1 to 3, the support members 12, 12', 12" of the heating members 6, 6', 6" may also function as or comprise an agitation means. To cause the agitation of the heating members 6, 6', 6", respective supporting members 12, 12', 12" may be vertically oscillated. This vertical oscillation of the supporting members 12, 12', 12" may cause the respective resilient members 10, 10', 10" to be compressed or stretched (depending on the direction of oscillation). This stretching or compressing of the resilient members 10, 10', 10" transfers the oscillatory motion of the supporting members 12, 12', 12" to respective heating members 6, 6', 6" to cause agitation of a sample, in use.

In alternative embodiments support members 12, 12', 12" may support more than one heating member 6, 6', 6". For instance, a single supporting member 12, 12', 12" may support a plurality of heating members 6 along well 18. In such embodiments, if the support members 12, 12', 12" also function as agitation means the oscillation of supporting member 12, 12', 12" results in the oscillation of each of the heating members 6, 6', 6" along the well 18. In such cases, the configuration provides a means to varying the agitation profile provided by the heating members as each row of heating members 6, 6', 6" may be agitated at different times or to different extents.

In further embodiments each of the heating members 6, 6', 6" within the well 18 may be operable to agitate a sample to a different extent. In embodiments wherein each of the heating members 6, 6', 6" within the well 18 are supported by a single supporting member 12, 12', 12", this differential agitation may be provided by providing resilient members 10, 10', 10" in each member 6, 6', 6" which comprise different spring constants. For example, at least one of the resilient members 10, 10', 10" may have a higher spring constant, i.e. it requires a greater force to compress or stretch than resilient members with a lower spring constant. In such cases, the heating member 6, 6', 6" comprising a resilient member 10, 10', 10" which has a higher spring constant will be agitated to a greater extent than the remaining heating members when the supporting member oscillates, whereas the other heating members within that row, i.e. those with resilient members having a lower spring constant, will be agitated to a lesser extent. This is due to the fact that resilient members having a higher spring constant will compress/stretch to a lesser extent upon movement of the supporting member 12, 12', 12" and hence transfer energy to the heating member 6, 6', 6" more readily than resilient members with a low spring constant where energy may dissipate due to the greater compression/stretching of the resilient member. In this way, specific heating members 6, 6', 6" can be chosen to be comprise resilient members 12, 12', 12" having a higher spring constant to define positions or individual members on the device having a higher agitation effect than other positions/members.

Figure 9:
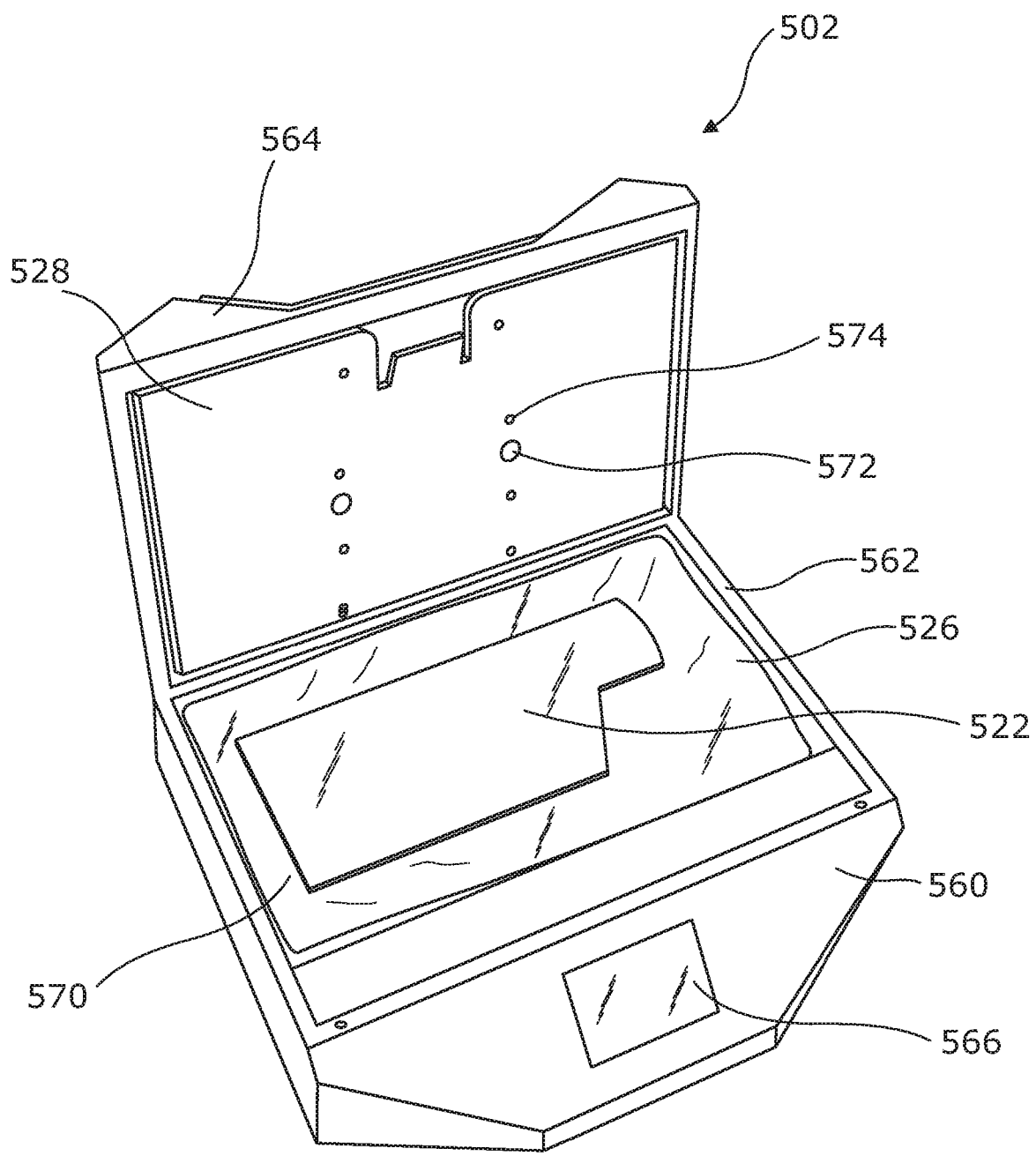
FIG. 9 shows a prototype device of the invention comprising upper and lower temperature sensors and an EVA cover to protect the device from contamination.
Figure 10:
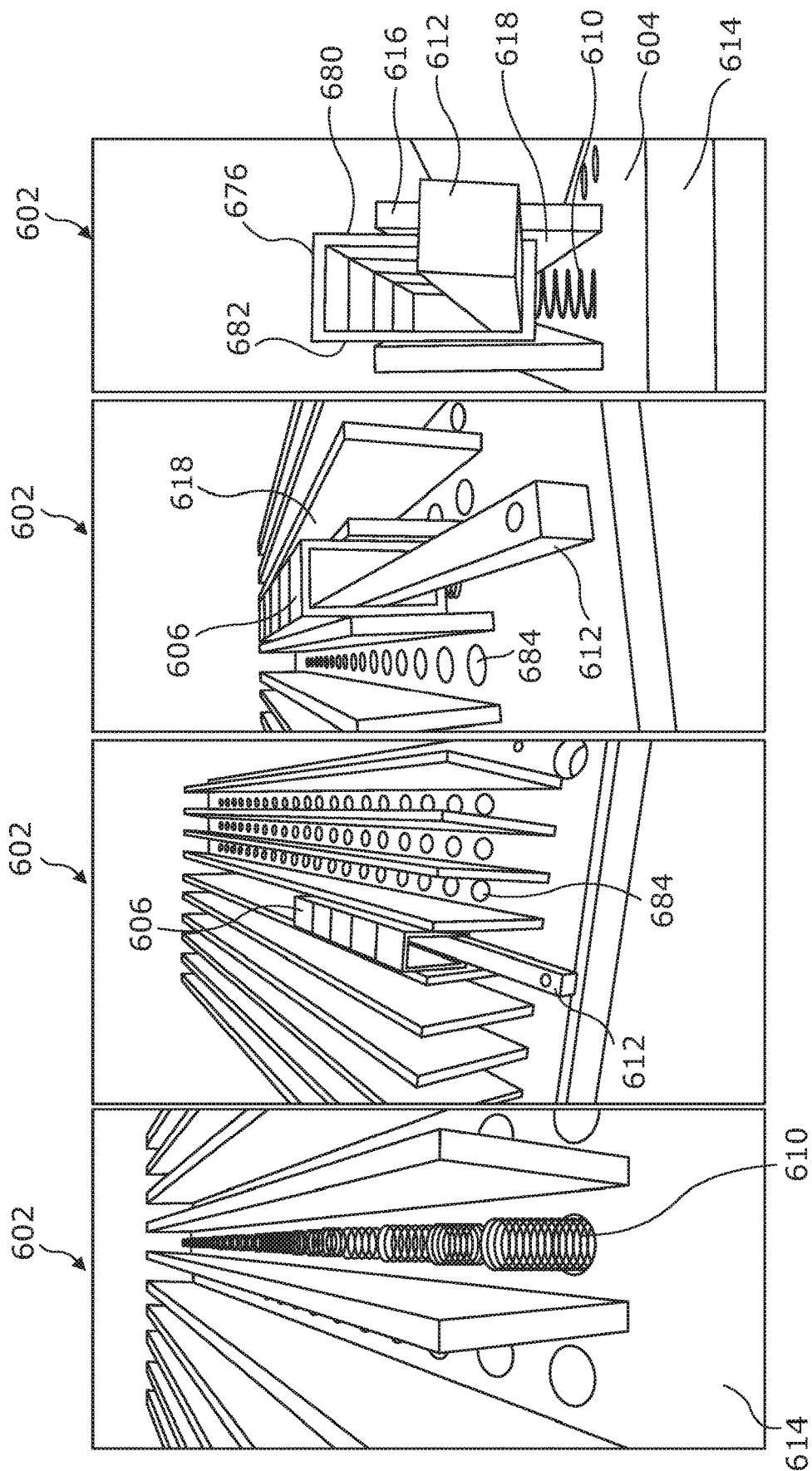

FIG. 9 illustrates an embodiment of a device 502 in accordance with an aspect of the invention. The device 502 has a housing 560 including a base 562 and a lid or cover 564 pivotally connected to the base. A heating plate and a plurality of heating members (not visible) are housed within the base together with a power supply unit and control electronics (also not visible). The control electronics includes a control screen 566 mounted in a front wall of the base. FIG. 9 shows a flexible membrane 526 positioned over heating members and a sample bag 522 in position on the membrane. The membrane may be an EVA cover similar to the membrane 426 described above in relation to FIGS. 7 & 8. The lid 564 includes a top plate 528 which presses on the bag 522 when the lid is closed to increase the force acting on the heating members and so ensure that a significant proportion of the heating members are in contact (indirectly) with the bag. The device 502 incorporates a lower temperature control sensor 570 in the base and an upper temperature control sensor in 572 in the lid. An IR temperature sensor 574 is also located in the lid.

In the embodiments described above, the resilient members 10, 310 are located within their respective heating members 306 and operative between an upper wall of the member and a support member 12 to keep the heating members spaced from the base plate 14 of the heating plate 4. In the embodiment as shown in FIG. 6, the resilient member 310 is in the form of a resiliently compressible material, though as previously stated the resilient member can be of any suitable form and could comprise a spring, such as a compression spring. FIGS. 10A to 10D illustrate an alternative embodiment of a device 602 for heating and/or cooling a sample in accordance with an aspect of the invention. FIGS. 10A to 10D show parts of the device in various stages of assembly.

The device 602 is similar to the previously described embodiments and has a heating/cooling plate 604 having a base plate 614 and a plurality of walls 616 extending upwardly from the base plate to define a series of wells 618 in the heating/cooling plate within which heating/cooling members 606 are located. The upstanding walls 616 are aligned parallel to one another and spaced apart so that the wells 618 are in the form of elongate channels, each channel receiving a plurality of heating/cooling members 606 aligned side-by-side in a row. The heating/cooling members 606 are elongate and generally rectangular parallelepiped in shape, having an upper wall 676, a lower wall 678, and a pair of opposed side walls 680, 682. At least the upper wall 676 and part of the side walls 680, 682 together define the contact surface 608. The heating/cooling members are aligned with the side walls 680, 682 adjacent the upstanding walls 616 for transfer of heat between the upstanding walls of the heating/cooling plate and the heating/cooling members 606. The other sides of the heating/cooling members 606 are open so as to leave a channel extending through all of the heating/cooling members in each row.

The device 602 differs from previous embodiments in that the resilient members 610 are in the form of coil springs acting in compression between the base plate 614 and the lower wall 678 of their respective heating/cooling member 606. A circular recess 684 is provided in the base plate 614 below each heating/cooling member 606 to locate a lower end of the spring 610 and a similar recess may be provided in the lower wall 678 of each heating/cooling member to locate the upper end the spring wall. Alternatively, projections may be provided on the base plate 614 and/or the lower wall 678 of each heating/cooling member about which the spring can be fitted to locate the ends of the springs. The springs 610 resiliently bias the heating cooling members 606 to the rest position and each heating/cooling member can be individually depressed from the rest position against the spring force. A support member 612 in the form of an elongate bar extends through all the heating/cooling members in each row. In use, the support member 612 is fixed at suitable position relative to the heating/cooling members. The support member 612 in this embodiment can be used to prevent the heating cooling members from falling out, in the event the device 602 is turned on its side or upside down. The support member 612 can also be used to prevent the heating/cooling members 606 being pressed into direct contact with the base plate 614 of the heating/cooling plate 604. In this case, the support member 612 is fixed at suitable position where it is engaged by the upper wall 676 of a heating/cooling element to prevent the lower wall 678 of the heating/cooling element touching the base plate 614. However, in some embodiments, it may be advantageous to allow the heating/cooling members to contact the base plate 614 in operation as this provided good thermal contact.

It will be appreciated that other arrangements for locating the springs 610 can be adopted and that the springs can engage with any suitable part of the heating/cooling members. The springs 610 may be made of any suitable material including, without limitation, metals such as spring steel and the like. In alternative embodiments, the springs 610 can be configured so that they prevent the heating/cooling members 606 engaging the base plate 614, in which case the support member bar 612 could be omitted. For example, the spring force may be sufficient to keep the heating/cooling member off the base plate 614 in use or the springs could be configured to become coil bound before the heating/cooling member touches the base plate 614. Similar spring arrangements to that illustrated in FIGS. 10A to 10D can be incorporated into the devices of any of the embodiments disclosed herein.

In addition to the individual heating/cooling members 6, 106, 206, 306, 406, 606 being resiliently biased, the frame or other supporting structure in which the heating/cooling members are located may be resiliently supported. This allows the device to compensate for a sample container which is more distorted than the plurality of heating/cooling members alone can compensate for. FIG. 11 illustrates one way in which this could be achieved.

FIG. 11 shows part of a device 702 in accordance with an aspect of the invention comprising a heating/cooling element 704 having a base plate 714 and upstanding walls 718 to define wells or cavities in which the heating/cooling members 706 are located. The heating/cooling element 704 is supported at each corner by means of a compression spring 786 (only one shown) and can be deflect downwardly against the bias of the springs 786 in response to a force (e.g. the presence of a sample/sample container on the plurality of members). The heating/cooling element 704 can be deflected evenly or unevenly so that the base plate 714 can tilt. Resiliently mounting the heating/cooling element 704 or other supporting structure in which the heating/cooling members are mounted allows the device 702 to compensate for a sample container which is more distorted than the plurality of movable heating/cooling members alone can compensate for. In use where a sample bag is highly distorted, the heating/cooling element 704 is deflected to provide a gross adjustment with the individual heating/cooling members allowing fine adjustment so as to maintain heating/cooling members in contact with as large a surface area of the sample as possible for even heating/cooling. Typically, it is expected that this feature will be of particular advantage in devices for thawing samples in bags from frozen, where the sample bag has frozen in a distorted shape.

The biasing means need not be springs 786 but can take any suitable form such as a resilient material (foam) and/or a gas spring, and a combination of different biasing means could be used. It should also be appreciated that any suitable number biasing means can be used, e.g. at least 1, 2, 3, 4, 5, 6, 7, 8, 9 or 10 biasing means. A similar resilient mounting of the heating/cooling element 4, 714 or other supporting structure for the heating/cooling elements can be adopted in any of the embodiments disclosed herein.

FIG. 12 illustrates an embodiment of an agitator 888 which can be incorporated into a device 2, 102, 202, 302, 402, 502, 602, 702 in accordance with an aspect of the invention.

The agitator 888 is a force-limited agitator comprising a support frame 890 on which is mounted an actuator 892 which drives a rotary shaft 894 in an oscillating, reciprocal rotary motion. The reciprocating oscillatory movement of the shaft 894 is imparted through a coil spring 896 to a pair of agitator pins 898 slidably mounted to the frame. Thus, as the shaft 894 oscillates, the agitator pins 896 are caused to move reciprocally in a liner direction. In use, the agitator may be positioned so that the agitator pins 8989 contact a sample bag located on the heating/cooling members, through the flexible membrane cover where present.

The force applied by the agitator 890 is limited by the spring 896 whose arms deflect if the force applied to the agitator pins exceeds a certain limit. If there is resistance to the movement of the agitator pins 898, say resulting from the sample being frozen, the spring arms will deflect so that the agitator pins are not driven. Accordingly, the spring relieved agitator is capable of applying force to a sample but may reduce the force or yield depending on the ice fraction present within a sample. Typically, when a frozen sample is present, the spring relieved agitator will not agitate the sample. This may be advantageous if a sample is provided in a container such as a bag, which may be damaged by agitation in a frozen state. In alternative embodiments, the agitator pins can be operatively connected to at least some of the heating/cooling members 6, 106, 206, 306, 406, 506, 606 of a device to cause the heating/cooling members to move and agitate a sample supported on them. The agitator pins could be connected with the heating/cooling plate 4, 104, 154, 304, 354, 604, 704 or with one or more support members 12, 612, for example, or by any other suitable arrangement.

In some embodiments of a device in accordance with an aspect of the invention, it may be advantageous for a sample to be positioned centrally in the array of heating/cooling members for heating/cooling. Where the sample is small relative to the overall number of heating/cooling members present in the array, the device may be adapted so that only a subset or group of the heating/cooling members is exposed on which the sample can be placed. There are various ways in which this could be achieved. In one embodiment, the overall array of heating/cooling members is divided into two or more groups by one or more dividing member(s) which is/are movable between operative and inoperative positions. The arrangement is configured so that when the dividing member(s) is/are in the operative position, they form a frame surrounding a group or subset of the heating/cooling members which can be used in heating/cooling a sample, whereas when the dividing member(s) is/are in their inoperative position the whole array of heating/cooling members, or at least a larger group, are exposed. For example, in a device having say 400 heating/cooling members arranged in an array comprising 20 rows of 20 heating/cooling members, a group of say 100 heating/cooling members arranged in 10 rows of 10 at the centre of the array may be separated from the heating/cooling members surrounding them by one or more movable dividing members which can be raised and lowered. When the dividing members are raised to an operative position, the group of heating/cooling members at the centre of the array is exposed within a frame defined by the dividing members and can be used the heat/cool a small sample which can be accommodated on the group. However, when the dividing members are lowered to an inoperative position, the whole for the array of heating/cooling members is exposed and can be used with a larger sample or with multiple samples.

The dividing members may be frame members and may form part of the supporting structure for the heating/cooling members. Where only a group of the heating/cooling members are exposed, the device can be configured so that only the heating/cooling members in the group are heated/cooled.

Where a sample is being heated/cooled on a subset of the heating/cooling members, a flexible membrane, such as the membrane 426 described above with relation to FIGS. 7 & 8, can be attached to the raised dividing members surrounding the subset. This allows the use of a smaller flexible membrane than would be required when the whole array is exposed for use. The dividing members thus form a frame about the subset. Other movable frame arrangements can be provided which enable a frame to be formed about one or more subsets of the array and/or about the whole array.

Devices in accordance with an aspect of the invention may incorporate at least one imaging system (not shown) to allow sample identification and/or post heat/cool imaging of a sample prior to removal. The system can also be adapted to identify use of a correct flexible membrane, when present. Such an imaging system can be placed at any suitable location within or on the device and particularly could be located within or on the lid or cover of the device, particularly on the surface of the lid or cover which in use will be adjacent to the plurality of members. The imaging system may comprise at least one barcode scanner and/or camera. Thus, a single imaging system may comprise a barcode scanner and a camera, or a selection of these components. A skilled person will appreciate that if multiple imaging systems are present within the device, each imaging system may be the same (e.g. may comprise the same components) or different (e.g. may comprise different combinations of components).

A barcode scanner could be used to detect the presence of a barcode which is positioned in front of the scanner, e.g. a barcode on a sample container and/or on a flexible membrane. Such barcode readers are available commercially (e.g. from Adafruit). Further, it is possible that a barcode reader may additionally be modified or controlled to be capable of taking a photographic image (i.e. to act as a camera), e.g. by controlling the imaging sensor. It may be desirable to obtain a photographic image of a sample after the application of heat or cooling in a device of the invention, to provide a record of the incubation.

At least one RFID module may also be incorporated into a device in accordance with an aspect of the invention and could be used with or without an imaging system. A RFID module would be capable of detecting the presence of a RFID tag on a sample container and/or on a flexible membrane to be used with the device. For example, each membrane may have a RFID tag which contains information relating to the type and/or size of the membrane and the RFID module used to interrogate the RFID tag on a flexible membrane when placed over the heating/cooling members to check that an appropriate flexible membrane is being used. In an embodiment where the array of heating/cooling members is dividable into one or more groups, different sized flexile membranes may be provided depending on whether the whole array or a small sub-group of the heating/cooling members is being used. Information relating to the size of a membrane can be recorded in the RFID tag and the RFID module could be used to confirm that an appropriately sized membrane is being used. Of course, other relevant information can be recorded in an RFID tag depending on the requirements of any given application.

FIGS. 13 and 14 illustrate experimental results obtained using a device of the present invention. The results shown are a comparison of a prior art technique involving submerging a frozen/preserved sample in a water bath at 37° C. and the use of a device of the present invention as a thawing device. The thawed sample in both cases comprised a biological sample containing a plurality of cells.

FIG. 13 shows the percentage of cells recovered through thawing of a sample using a device of the present invention ("Beta Bag Thawer"), and immersion of a sample in water at 37° C. ("37 C Water"). As shown, the percentage of cells recovered in each case were roughly identical, within standard error, at around 75%.

FIG. 14 shows the percentage of proliferating cells present in a sample subsequent to thawing of the sample using a device of the present invention ("Beta Bag Thawer"), and immersion of a sample in water at 37° C. ("37 C Water"). As shown, the percentage of proliferating cells present in the sample in each case were roughly identical, within standard error, at around 60-65%.

FIG. 15 shows the percentage of proliferating cells present in a sample subsequent to thawing of the sample using a device of the present invention ("Beta Bag Thawer") and using a Plasmatherm device (Barkey). Standard deviation was measured for three thawed bags, where T tests for both assays showed no significant different.

FIG. 16 similarly shows that there is no significant difference in % viable cell recovery between using a water bath and a device of the present invention ("Via Thaw") for thawing T cells in volumes of either 10 or 20 mls. Three replicates of each volume were carried out in each device. The error bars represent standard deviation from 3 bag thaws. Cells had >95% viability in all conditions. Lower recovery was observed from 10 mL bags compared to 20 mL bags due to losses in tubing. The P value was 0.94 for 10 mL Via Thaw and 0.22 for 20 mL Via Thaw.

FIG. 17 shows the results obtained for testing the twenty four hour post-thaw cell viability of hepatocytes cryopreserved in CS50 cryobags thawed using a device of the invention. The results show that at least 70% viability levels were obtained. Four samples with bag codes B, C, D and E were tested.

The experimental results obtained show that the device of the present invention is at least as effective as prior art submersion techniques when used as a thawing device. A major advantage of the present invention over such prior art techniques is that the device is a 'dry' device and therefore the risk of contamination of the sample is greatly reduced when the need to submerge the sample is removed. In addition, devices and methods of the present invention may be used to highly selectively agitate and heat/cool samples or specific regions of samples, as opposed to the bulk heating/cooling of samples using submersion techniques.

The above embodiments are described by way of example only. Many variations are possible without departing from the scope of the invention as defined in the appended claims.

The invention claimed is:

1. A device for heating or cooling one or more samples, the device comprising a heat source or a cold source, a plurality of members operable in use to heat and/or cool one or more samples, each of the plurality of members comprising a sample contact surface and a biasing means, wherein, in use: each member is biased towards a resting position under the operation of said biasing means and is independently moveable with respect to each of the remaining members against said bias under the application of a force on the sample contact surface wherein two or more members are provided in a first dimension of a plane and aligned to move perpendicular to the plane and two or more of the members are provided in a second dimension of the plane and aligned to move perpendicular to the plane, wherein the plurality of members are provided (i) in a horizontal plane onto which a sample or sample container may be placed, in use, with one or more of the plurality of members being aligned so as to move vertically with respect to the horizontal plane, or (ii) in a vertical plane against which a sample may be placed, in use, with one or more of the plurality of members being aligned so as to move horizontally with respect to the vertical plane.

2. The device as claimed in claim 1 wherein the members are operable in use to conduct heat energy from the heat source or the cold source.

3. The device as claimed in claim 2 wherein the device comprises a heat source and the heat source comprises a heating element.

4. The device as claimed in claim 3 wherein the heating or cooling element comprises a series of wells or cavities within which one or more of the plurality of members may move, in use.

5. The device as claimed in claim 4 wherein each of the series of wells or cavities comprises a single member.

6. The device as claimed in claim 2 wherein one or more of the plurality of members is thermally connected to the heat source or the cold source.

7. The device as claimed in claim 6 wherein the device comprises a conductive material, or an air gap, between one or more of said plurality of members and said heat source or said cold source.

8. The device as claimed in claim 1 wherein the members are operable in use to conduct heat energy from one or more samples in order to reduce the temperature of one or more samples.

9. The device as claimed in claim 1 comprising a cooled material, the cooled material being operable in use to flow through and/or in the members and conduct heat energy from the members in order to reduce the temperature thereof.

10. The device as claimed in claim 1 wherein the biasing means is operable to maintain an air gap between the corresponding member and the heat source or the cold source.

11. The device as claimed in claim 1 wherein each member comprises a sample contact surface which, in use, contacts a portion of a sample to transfer heat energy to or conduct heat energy from a sample.

12. The device as claimed in claim 1 wherein two or more of the plurality of members are arranged to form one or more tubular recesses into which one or more samples or sample containers are placed, in use, with the sample contact surfaces of two or more members defining the walls of the or each recess.

13. The device as claimed in claim 1 operable to temporally and/or spatially differentially heat or cool a sample or samples, in use, wherein said device comprises at least one heating or cooling element.

14. The device as claimed in claim 1 comprising a means to agitate a sample or samples, in use, during the heating or cooling process.

15. The device as claimed in claim 14 operable in use to temporally or spatially control the agitation provided.

16. The device as claimed in claim 1 comprising one or more sensors operable in use to monitor one or more characteristics of the members, and/or a sample, and/or the container within which a sample is contained.

17. The device as claimed in claim 16 wherein the one or more sensors comprise temperature sensors operable in use to monitor the temperature of one or more of the members, a sample, or at least one or more regions within a sample, the container within which a sample is contained, or at least one or more regions within the container, and/or structural sensors operable in use to determine the ice fraction of a sample.

18. The device as claimed in claim 1 wherein one or more of the plurality of members comprises a substantially elongate structure.

19. The device as claimed in claim 18 wherein one or more of the plurality of members comprises a pin.

20. The device as claimed in claim 1 wherein the biasing means comprises a compression spring, or a resilient material which is resiliently deformable under the application of a force.

21. The device as claimed in claim 1 wherein at least one of the members additionally comprises a supporting member which is operable in use to control the extent to which the corresponding member may be moved against the bias provided by the biasing means.

22. The device of claim 1 comprising a flexible membrane positioned over at least a portion of the sample contact surface of one or more of the plurality of members.

23. The device of claim 22 wherein the flexible membrane comprises a thermally conductive material.

24. The device as claimed in claim 1 wherein the plurality of members are located on a supporting structure which itself is resiliently biased to a resting position and is moveable against said bias under the application of a force on the sample contact surface.

25. The device of claim 1, wherein the device comprises a cold source and the cold source comprises a cooling element.

26. A method of heating or cooling one or more samples comprised within a container, the method comprising contacting the container with one or more of a plurality of members, wherein said one or more of the plurality of members in contact with said sample provide a source of heat energy to the container to heat the sample contained therein, or conduct heat energy from the container to cool the sample contained therein, wherein each of the plurality of members are biased towards a resting position and are independently moveable with respect to one another against said bias to a position wherein two or more members are provided in a first dimension of a plane and aligned to move perpendicular to the plane and two or more of the members are provided in a second dimension of the plane and aligned to move perpendicular to the plane, wherein the plurality of members are provided (i) in a horizontal plane onto which a sample or sample container may be placed, in use, with one or more of the plurality of members being aligned so as to move vertically with respect to the horizontal plane, or (ii) in a vertical plane against which a sample may be placed, in use, with one or more of the plurality of members being aligned so as to move horizontally with respect to the vertical plane.

27. The method as claimed in claim 26 comprising spatially or temporally differentially heating or cooling the sample by independently controlling the heat energy transferred to or from each member, or group of members.

28. The method as claimed in claim 26 comprising agitating the sample.

29. The method as claimed in claim 26 comprising monitoring one or more characteristics of the members, and/or the sample, and/or the container within which the sample is contained.

30. The method as claimed in claim 29 comprising adjusting the heating/cooling profile and/or the agitating of the sample in response to the monitored characteristics.

* * * * *